US012648880B2

(12) United States Patent
Rice et al.

(10) Patent No.: US 12,648,880 B2
(45) Date of Patent: Jun. 9, 2026

(54) DRESSING WITH PROTRUDING LAYER ALLOWING FOR CLEANSING OF WOUND BED MACRO DEFORMATIONS

(71) Applicant: Solventum Intellectual Properties Company, Maplewood, MN (US)

(72) Inventors: Justin Rice, San Antonio, TX (US); Christopher Allen Carroll, San Antonio, TX (US); Shannon C. Ingram, Bulverde, TX (US)

(73) Assignee: Solventum Intellectual Properties Comapny, Maplewood, MN (US)

( * ) Notice: Subject to any disclaimer, the term of this patent is extended or adjusted under 35 U.S.C. 154(b) by 0 days.

(21) Appl. No.: 16/678,292

(22) Filed: Nov. 8, 2019

(65) Prior Publication Data

US 2020/0146896 A1 May 14, 2020

Related U.S. Application Data

(60) Provisional application No. 62/757,503, filed on Nov. 8, 2018.

(51) Int. Cl.
| | |
|---|---|
| *A61F 13/00* | (2006.01) |
| *A61B 17/32* | (2006.01) |
| *A61F 13/02* | (2006.01) |
| *A61F 13/05* | (2024.01) |
| *A61M 1/00* | (2006.01) |

(52) U.S. Cl.
CPC ............. *A61F 13/05* (2024.01); *A61B 17/32* (2013.01); *A61F 13/02* (2013.01); *A61M 1/915* (2021.05); *A61F 2013/00174* (2013.01);

*A61F 2013/00327* (2013.01); *A61M 1/85* (2021.05); *A61M 1/92* (2021.05)

(58) Field of Classification Search
CPC ................ A61F 13/00068; A61F 13/02; A61F 2013/00174; A61F 2013/00327; A61M 1/0088

See application file for complete search history.

(56) References Cited

U.S. PATENT DOCUMENTS

| | | | |
|---|---|---|---|
| 1,355,846 | A | 10/1920 | Rannells |
| 2,547,758 | A | 4/1951 | Keeling |
| 2,632,443 | A | 3/1953 | Lesher |
| 2,682,873 | A | 7/1954 | Evans et al. |

(Continued)

FOREIGN PATENT DOCUMENTS

| | | | |
|---|---|---|---|
| AU | 550575 | B2 | 3/1986 |
| AU | 745271 | B2 | 3/2002 |

(Continued)

OTHER PUBLICATIONS

International Search Report and Written Opinion for Corresponding Application No. PCT/US2019/060479, dated Apr. 7, 2020.

(Continued)

*Primary Examiner* — Jessica Arble
*Assistant Examiner* — Nhu Q. Tran

(57) ABSTRACT

A dressing that includes a contact layer having walls defining a plurality of holes and a retainer layer comprising portions protruding into holes of a contact layer is provided herein. Systems, methods and kits using the dressing for debriding a tissue site are also provided herein.

10 Claims, 9 Drawing Sheets

110

(56) References Cited

U.S. PATENT DOCUMENTS

| | | | |
|---|---|---|---|
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,683,921 | A | 8/1972 | Brooks et al. |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,902,565 | A | 2/1990 | Brook |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,765,123 | B2 | 7/2004 | de Jong et al. |
| 6,814,079 | B2 | 11/2004 | Heaton et al. |
| 7,381,859 | B2 | 6/2008 | Hunt et al. |
| 7,846,141 | B2 | 12/2010 | Weston |
| 7,951,124 | B2 | 5/2011 | Boehringer et al. |
| 8,062,273 | B2 | 11/2011 | Weston |
| 8,216,198 | B2 | 7/2012 | Heagle et al. |
| 8,251,979 | B2 | 8/2012 | Malhi |
| 8,257,327 | B2 | 9/2012 | Blott et al. |
| 8,398,614 | B2 | 3/2013 | Blott et al. |
| 8,449,509 | B2 | 5/2013 | Weston |
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,679,081 | B2 | 3/2014 | Heagle et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| 9,168,180 | B2 | 10/2015 | Ha et al. |
| 9,198,801 | B2 | 12/2015 | Weston |
| 9,211,365 | B2 | 12/2015 | Weston |
| 9,289,542 | B2 | 3/2016 | Blott et al. |
| 9,421,309 | B2 | 8/2016 | Robinson et al. |
| 9,918,733 | B2 | 3/2018 | Ingram et al. |
| 9,974,694 | B2 | 5/2018 | Locke et al. |
| 10,369,058 | B2 | 8/2019 | Ha et al. |
| 10,610,414 | B2 | 4/2020 | Hartwell et al. |
| 10,736,788 | B2 | 8/2020 | Locke et al. |
| 10,743,900 | B2 | 8/2020 | Ingram et al. |
| 11,224,542 | B2 | 1/2022 | Robinson et al. |
| 2001/0037118 | A1 | 11/2001 | Shadduck |
| 2002/0065494 | A1 | 5/2002 | Lockwood et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2002/0161346 | A1 | 10/2002 | Lockwood et al. |
| 2004/0030304 | A1 | 2/2004 | Hunt et al. |
| 2005/0282895 | A1 | 12/2005 | Dosch et al. |
| 2007/0185426 | A1 | 8/2007 | Ambrosio et al. |
| 2008/0132819 | A1 | 6/2008 | Radl et al. |
| 2008/0177253 | A1 | 7/2008 | Boehringer et al. |
| 2008/0275409 | A1 | 11/2008 | Kane et al. |
| 2008/0300555 | A1* | 12/2008 | Olson ............... A61F 13/00068 |
| | | | 604/313 |
| 2009/0012482 | A1 | 1/2009 | Pinto et al. |
| 2009/0093779 | A1 | 4/2009 | Riesinger |
| 2009/0227969 | A1 | 9/2009 | Jaeb et al. |
| 2009/0299303 | A1 | 12/2009 | Seegert |
| 2010/0063484 | A1 | 3/2010 | Heagle |
| 2010/0160871 | A1 | 6/2010 | Seegert et al. |
| 2010/0160874 | A1* | 6/2010 | Robinson ............. A61M 1/915 |
| | | | 604/319 |
| 2010/0160876 | A1 | 6/2010 | Robinson et al. |
| 2010/0185163 | A1 | 7/2010 | Heagle |
| 2010/0312159 | A1 | 12/2010 | Aali et al. |
| 2011/0015619 | A1 | 1/2011 | Svedman et al. |

(56) References Cited

U.S. PATENT DOCUMENTS

| | | |
|---|---|---|
| 2011/0054422 A1 | 3/2011 | Locke et al. |
| 2011/0087176 A2 | 4/2011 | Blott et al. |
| 2011/0118683 A1 | 5/2011 | Weston |
| 2011/0178451 A1 | 7/2011 | Robinson et al. |
| 2011/0213287 A1 | 9/2011 | Lattimore et al. |
| 2011/0213319 A1 | 9/2011 | Blott et al. |
| 2011/0230809 A1 | 9/2011 | Manwaring et al. |
| 2011/0282309 A1 | 11/2011 | Adie et al. |
| 2011/0301556 A1 | 12/2011 | Lichtenstein |
| 2012/0016334 A1 | 1/2012 | Nakajima et al. |
| 2012/0143113 A1* | 6/2012 | Robinson ................ A61M 1/85 |
| | | 602/43 |
| 2012/0143114 A1 | 6/2012 | Locke et al. |
| 2012/0157945 A1 | 6/2012 | Robinson et al. |
| 2013/0072850 A1* | 3/2013 | Locke ..................... A61L 15/22 |
| | | 604/20 |
| 2013/0144230 A1 | 6/2013 | Wu et al. |
| 2013/0211349 A1 | 8/2013 | Stokes et al. |
| 2013/0274717 A1 | 10/2013 | Dunn |
| 2014/0066868 A1 | 3/2014 | Freedman et al. |
| 2014/0155791 A1 | 6/2014 | Robinson et al. |
| 2014/0163491 A1 | 6/2014 | Schuessler et al. |
| 2014/0228787 A1 | 8/2014 | Croizat et al. |
| 2014/0236112 A1 | 8/2014 | Von Wolff et al. |
| 2015/0080788 A1 | 3/2015 | Blott et al. |
| 2015/0119832 A1 | 4/2015 | Locke |
| 2015/0174284 A1 | 6/2015 | Payne et al. |
| 2015/0201954 A1 | 7/2015 | Pratt et al. |
| 2015/0320434 A1 | 11/2015 | Ingram et al. |
| 2015/0320602 A1 | 11/2015 | Locke et al. |
| 2015/0320603 A1 | 11/2015 | Locke et al. |
| 2016/0022885 A1 | 1/2016 | Dunn et al. |
| 2016/0038345 A1 | 2/2016 | Ha et al. |
| 2016/0095754 A1 | 4/2016 | Andrews et al. |
| 2016/0158066 A1 | 6/2016 | Chao |
| 2016/0175156 A1 | 6/2016 | Locke et al. |
| 2016/0354086 A1 | 12/2016 | Dunn |
| 2017/0007462 A1 | 1/2017 | Hartwell et al. |
| 2017/0135862 A1 | 5/2017 | Tuck et al. |
| 2017/0189237 A1 | 7/2017 | Locke et al. |
| 2017/0197006 A1 | 7/2017 | Johnson et al. |
| 2017/0231822 A1 | 8/2017 | Hoggarth et al. |
| 2017/0239095 A1 | 8/2017 | Hoggarth et al. |
| 2018/0235646 A1 | 8/2018 | Locke et al. |
| 2018/0353337 A1 | 12/2018 | Locke |
| 2018/0353338 A1 | 12/2018 | Locke et al. |
| 2018/0353662 A1 | 12/2018 | Locke et al. |
| 2019/0117465 A1 | 4/2019 | Osborne et al. |
| 2019/0192350 A1 | 6/2019 | Gowans et al. |
| 2019/0231944 A1 | 8/2019 | Dunn et al. |
| 2019/0274889 A1 | 9/2019 | Steward et al. |
| 2019/0314209 A1 | 10/2019 | Ha et al. |
| 2020/0046567 A1 | 2/2020 | Carroll et al. |
| 2020/0107965 A1 | 4/2020 | Greener |
| 2020/0146896 A1 | 5/2020 | Rice et al. |
| 2020/0155359 A1 | 5/2020 | Carroll et al. |
| 2020/0383837 A1 | 12/2020 | Gowans et al. |
| 2021/0077302 A1 | 3/2021 | Carroll et al. |
| 2021/0228417 A1 | 7/2021 | Ha et al. |
| 2023/0000687 A1 | 1/2023 | Rice et al. |
| 2023/0000688 A1 | 1/2023 | Rice et al. |
| 2024/0099898 A1 | 3/2024 | Rice et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| DE | 102006017194 A1 | 10/2007 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 2098257 A1 | 9/2009 |
| EP | 3263079 A1 | 1/2018 |
| EP | 3378450 A1 | 9/2018 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| GB | 2365350 A | 2/2002 |
| GB | 2377939 A | 1/2003 |
| JP | S57-013040 A | 1/1982 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 0185248 A1 | 11/2001 |
| WO | 2005102234 A2 | 11/2005 |
| WO | 2006114638 A2 | 11/2006 |
| WO | 2008/005532 A2 | 1/2008 |
| WO | 2008136998 A1 | 11/2008 |
| WO | 2009021523 A1 | 2/2009 |
| WO | 2009/146441 A1 | 12/2009 |
| WO | 2010051071 A1 | 5/2010 |
| WO | 2010051073 A1 | 5/2010 |
| WO | 2010075178 A2 | 7/2010 |
| WO | 2011008497 A2 | 1/2011 |
| WO | 2011089098 A1 | 7/2011 |
| WO | 2013/032745 A1 | 3/2013 |
| WO | 2013066426 A2 | 5/2013 |
| WO | 2013071243 A2 | 5/2013 |
| WO | 2013116552 A1 | 8/2013 |
| WO | 2013129343 A1 | 9/2013 |
| WO | 2013149078 A1 | 10/2013 |
| WO | 2014/014922 A1 | 1/2014 |
| WO | 2014014871 A1 | 1/2014 |
| WO | 2014024048 A1 | 2/2014 |
| WO | 2014143487 A1 | 9/2014 |
| WO | 2015172104 A1 | 11/2015 |
| WO | 2015172111 A1 | 11/2015 |
| WO | 2015173547 A1 | 11/2015 |
| WO | 2017195038 A1 | 11/2017 |
| WO | 2018/077872 A1 | 5/2018 |
| WO | 2018/094061 A1 | 5/2018 |
| WO | 2018/226328 A1 | 12/2018 |
| WO | 2019136164 A1 | 7/2019 |
| WO | 2019152422 A1 | 8/2019 |
| WO | 2020097529 A1 | 5/2020 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

(56)　　　　　References Cited

OTHER PUBLICATIONS

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax, " Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

Partial International Search Report from PCT/US2015/030030 dated Jul. 22, 2015.

International Search Report and Written Opinion for PCT/US2015/030023 dated Aug. 24, 2015.

Extended European Search Report for corresponding Application No. 171862527, dated Nov. 14, 2017.

"Introduction to Polyurethanes: Thermoplastic Polyurethane", American Chemistry Council, 2018, https://polyurethane.americanchemistry.com/polyurethanes/Introduction-to-Polyurethanes/Applications/Thermoplastic-Polyurethane/.

International Search Report and Written Opinion for PCT/US2015/030027 dated Jul. 15, 2015.

International Search Report and Written Opinion for corresponding Application No. PCT/US2019/027463, dated Jul. 1, 2019.

Japanese Notice of Rejection for corresponding Application No. 2016-566815, dated Feb. 5, 2019.

Extended European Search Report for corresponding Application No. 18162504.7, dated May 24, 2018.

Japanese Notice of Rejection for corresponding Application No. 2016-566785, dated Jun. 25, 2019.

Japanese Notice of Rejection for corresponding Application No. 2016-566785, dated Jan. 29, 2019.

Non-Final Office Action for Corresponding U.S. Appl. No. 15/960,310, dated Apr. 29, 2020.

Japanese Notice of Rejection for Corresponding Application No. 2019-233695, dated Oct. 13, 2020.

International Search Report and Written Opinion for Corresponding Application No. PCT/US2019/060567, dated Feb. 14, 2020.

International Search Report and Written Opinion for Corresponding Application No. PCT/US2019/045505, dated Nov. 7, 2019.

International Search Report and Written Opinion for Corresponding Application No. PCT/US2020/013922, dated May 4, 2020.

Chinese Notice of Rejection Corresponding to Application No. 2020800099951, dated Mar. 28, 2022.

International Search Report and Written Opinion for Corresponding Application No. PCT/IB2020/056911, dated Oct. 21, 2020.

(56) References Cited

OTHER PUBLICATIONS

International Search Report and Written Opinion Corresponding to Application No. PCT/IB2020/061435, dated Mar. 16, 2021.
International Search Report and Written Opinion Corresponding to Application No. PCT/IB2020/061465, dated Mar. 16, 2021.
International Search Report and Written Opinion Corresponding to Application No. PCT/IB2020/061540, dated Feb. 24, 2021.
Canadian Examination Report for related application 2,947,302, dated Jun. 11, 2021.
Japanese Notice of Rejection for related application 2020-557257, dated Feb. 28, 2023.
Office Action for related U.S. Appl. No. 16/678,450, dated Jul. 31, 2023.
Office Action for related U.S. Appl. No. 16/923,651, dated Aug. 28, 2023.
Office action for related U.S. Appl. No. 16/918,682, dated Sep. 21, 2023.
Japanese Notice of Rejection for Application No. 2021-542412, dated Dec. 5, 2023.
European Examination Report for Application No. 20747133.5, dated Dec. 21, 2023.
Office Action for related U.S. Appl. No. 16/923,651 dated Feb. 12, 2024.
Japanese Notice of Rejection for Application No. 2019-233695 dated Mar. 5, 2024.
Office Action for related U.S. Appl. No. 17/629,174, dated Mar. 26, 2024.
Japanese Notice of Rejection for Application No. 2021-524440 dated Apr. 16, 2024.
Office action for U.S. Appl. No. 16/678,450, dated Sep. 9, 2024.
Office action for U.S. Appl. No. 16/745,075, dated Jul. 24, 2024.
Japanese Decision of Rejection and Decision for Dismissal of Amendment for Application No. 2021-524440, dated Oct. 15, 2024.
Office action for U.S. Appl. No. 16/918,682, dated Jan. 2, 2025.
Copper Development Association Inc., Introduction to Antimicrobial Copper, Feb. 15, 2024.
Office action for U.S. Appl. No. 17/629,174, dated Feb. 26, 2025.
Office action for U.S. Appl. No. 17/779,755, dated Apr. 9, 2025.
Office action for U.S. Appl. No. 17/779,792, dated Jun. 3, 2025.
Office Action for related U.S. Appl. No. 18/538,282, dated Nov. 10, 2025.
Office Action for related U.S. Appl. No. 17/779,755, dated Jan. 8, 2026.
Office Action for corresponding U.S. Appl. No. 16/745,075, dated Jan. 28, 2026.

* cited by examiner

FIG. 10

DRESSING WITH PROTRUDING LAYER ALLOWING FOR CLEANSING OF WOUND BED MACRO DEFORMATIONS

RELATED APPLICATIONS

This application claims the benefit, under 35 U.S.C. § 119(e), of the filing of U.S. Provisional Patent Application Ser. No. 62/757,503, entitled "Dressing With Protruding Layer Allowing For Cleansing Of Wound Bed Macro Deformations," filed Nov. 8, 2018, which is incorporated herein by reference for all purposes.

TECHNICAL FIELD

The invention set forth in the appended claims relates generally to tissue treatment systems and more particularly, but without limitation, to debridement dressings and methods and systems for debriding tissue using the debridement dressings.

BACKGROUND

A wide variety of materials and devices, generally characterized as "dressings," are generally known in the art for use in treating a wound or other disruption of tissue. Such wounds may be the result of trauma, surgery, or disease, and may affect skin or other tissues. In general, dressings may control bleeding, absorb wound exudate, ease pain, protect wound tissue from infection, or otherwise promote healing and protect the wound from further damage.

Debriding tissue can also be beneficial for wound healing. For example, removing necrotic tissue, biofilm, slough, eschar, and other debris from a wound can improve the efficacy and efficiency of various treatments and dressings, and reduce the risk of infection.

Additionally, clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound can be washed out with a stream of liquid solution, or a cavity can be washed out using a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy, debridement, and instillation therapy are known, improvements to therapy systems, components, and processes may benefit healthcare providers and patients.

BRIEF SUMMARY

Apparatuses, systems and methods for treating tissue in a negative-pressure therapy environment are set forth in the appended claims. Illustrative embodiments are also provided to enable a person skilled in the art to make and use the claimed subject matter.

For example, in some embodiments, an apparatus for treating a tissue site with negative pressure may comprise a dressing that can improve slough removal with macro-deformations to the tissue site. In certain embodiments, the dressing may comprise a contact layer with holes, a retainer layer with portions protruding into holes of the contact layer, a cover layer, and optionally a filler layer.

More generally, a dressing may be provided for treating a tissue site with negative pressure. The dressing may comprise a contact layer, which can comprise a first manifold having a plurality of holes through the first manifold. The dressing may also comprise a retainer layer comprising a second manifold having a plurality of projections, at least some of the projections protruding into at least some of the plurality of holes. In some embodiments, the second manifold may be more compressible than the first manifold. The plurality of projections may be complementary to the plurality of holes in some embodiments. For example, at least some projections may have a size and profile that is complementary to that of at least some holes, or fill at least some holes partially (for example, at least 50% or 90%).

Alternatively, other example embodiments may include a debridement apparatus. The debridement apparatus may comprise a manifold having a side configured to be positioned adjacent to a tissue site. The apparatus may further comprise a plurality of recesses in the side configured to be positioned adjacent to a tissue site. In some examples, projections may also be disposed within one or more of the recesses. The manifold can be configured to collapse the recesses from a relaxed position to a contracted position in response to negative pressure.

Debridement methods are also described herein, wherein some example embodiments include positioning a contact layer adjacent a tissue site, the contact layer comprising a plurality of holes; positioning a retainer layer over the contact layer, the retainer layer comprising a plurality of projections extending into the plurality of holes; and applying negative pressure to the tissue site. Under negative pressure, slough can be removed through the plurality of holes, and the projections can contact tissue drawn into the plurality of holes. In some embodiments, the contact layer can be configured to collapse the plurality of holes from a relaxed position to a contracted position in response to the negative pressure, which can cause macro-deformation at the tissue site.

Alternatively, other methods of debridement may comprise positioning a contact layer adjacent to a tissue site, the contact layer comprising a plurality of recesses and applying negative pressure to the contact layer, wherein the contact layer is configured to collapse the plurality of recesses from a relaxed position to a contracted position in response to the negative pressure, which can cause macro-deformation at the tissue site and can remove slough from the tissue site. In some examples, projections may also be disposed in the recesses and configured to contact tissue drawn into the recesses.

Objectives, advantages, and a preferred mode of making and using the claimed subject matter may be understood best by reference to the accompanying drawings in conjunction with the following detailed description of illustrative embodiments.

BRIEF DESCRIPTION OF THE DRAWINGS

FIG. 10 is a plan view of the contact layer of FIG. 3 contracting under negative pressure.

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

I. Therapy System

Figure 1:
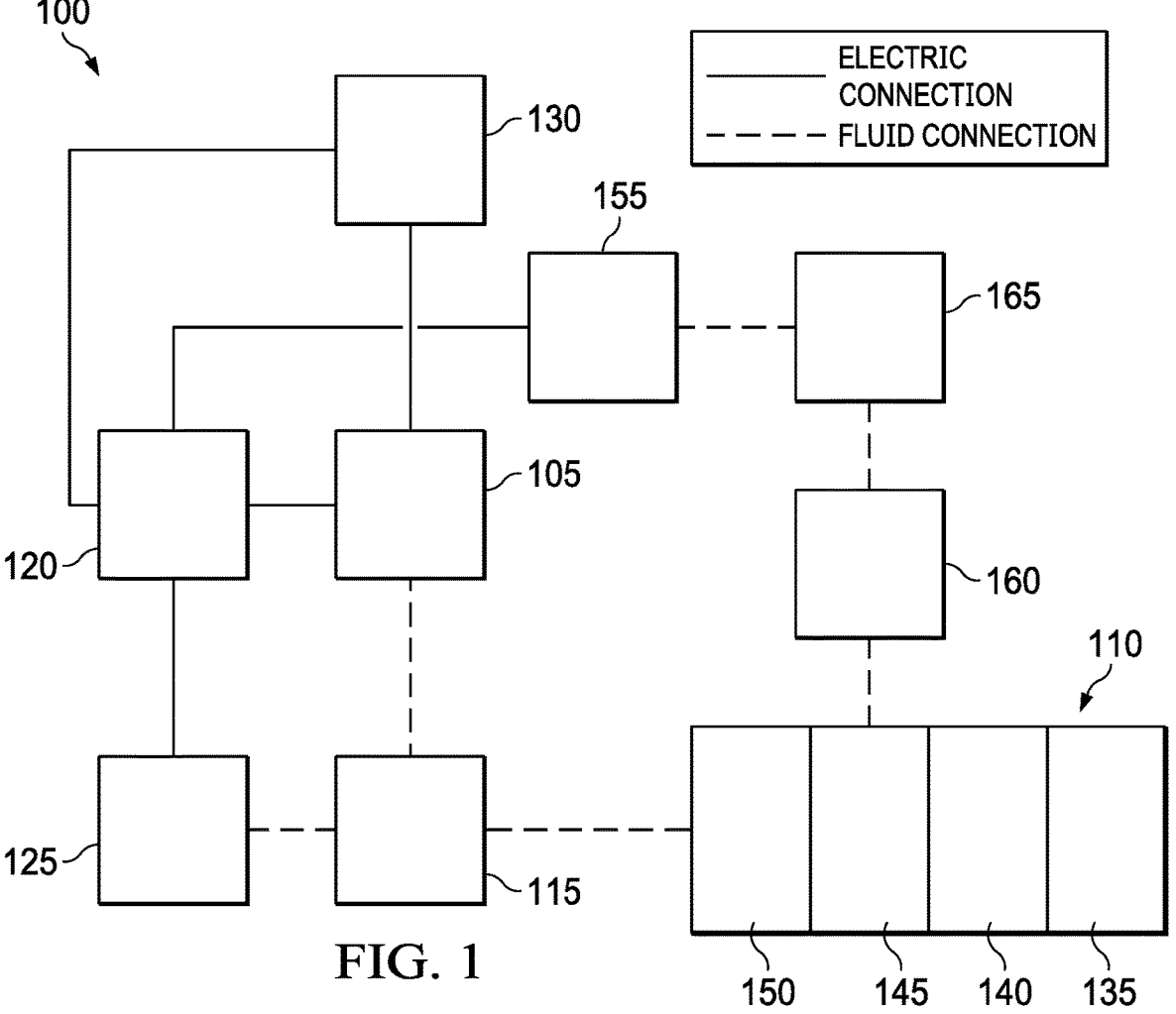
FIG. 1 is a functional block diagram of an example embodiment of a therapy system that can treat tissue in accordance with this specification.

FIG. 1 is a simplified functional block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 105, a dressing 110, a fluid container, such as a container 115, and a regulator or controller, such as a controller 120, for example. Additionally, the therapy system 100 may include sensors to measure operating parameters and provide feedback signals to the controller 120 indicative of the operating parameters. As illustrated in FIG. 1, for example, the therapy system 100 may include a first sensor 125, a second sensor 130, or both, coupled to the controller 120. As illustrated in the example of FIG. 1, the dressing 110 may comprise or consist essentially of some combination of a debriding matrix 135, a contact layer 140, a retainer layer 145, and a cover layer 150.

The therapy system 100 may also include a source of instillation solution. For example, a solution source 165 may be fluidly coupled to the dressing 110, as illustrated in the example embodiment of FIG. 1. The solution source 165 may be fluidly coupled to a positive-pressure source such as the positive-pressure source 155, a negative-pressure source such as the negative-pressure source 105, or both in some embodiments. A regulator, such as an instillation regulator 160, may also be fluidly coupled to the solution source 165 and the dressing 110 to ensure proper dosage of instillation solution (e.g., saline) to a tissue site. For example, the instillation regulator 160 may comprise a piston that can be pneumatically actuated by the negative-pressure source 105 to draw instillation solution from the solution source during a negative-pressure interval and to instill the solution to a dressing during a venting interval. Additionally or alternatively, the controller 120 may be coupled to the negative-pressure source 105, the positive-pressure source 155, or both, to control dosage of instillation solution to a tissue site. In some embodiments, the instillation regulator 160 may also be fluidly coupled to the negative-pressure source 105 through the dressing 110, as illustrated in the example of FIG. 1.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the solution source 165, the controller 120 and other components into a therapy unit.

In general, components of the therapy system 100 may be coupled directly or indirectly. For example, the negative-pressure source 105 may be directly coupled to the container 115, and may be indirectly coupled to the dressing 110 through the container 115. Coupling may include fluid, mechanical, thermal, electrical, or chemical coupling (such as a chemical bond), or some combination of coupling in some contexts. For example, the negative-pressure source 105 may be electrically coupled to the controller 120, and may be fluidly coupled to one or more distribution components to provide a fluid path to a tissue site. In some embodiments, components may also be coupled by virtue of physical proximity, being integral to a single structure, or being formed from the same piece of material.

A distribution component may be detachable, or may be disposable, reusable, or recyclable. The dressing 110 and the container 115 are illustrative of distribution components. A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 110. For example, such a dressing interface may be a SENSA-T.R.A.C.™ Pad available from KCI of San Antonio, Tex.

A. Dressing

Figure 2A:
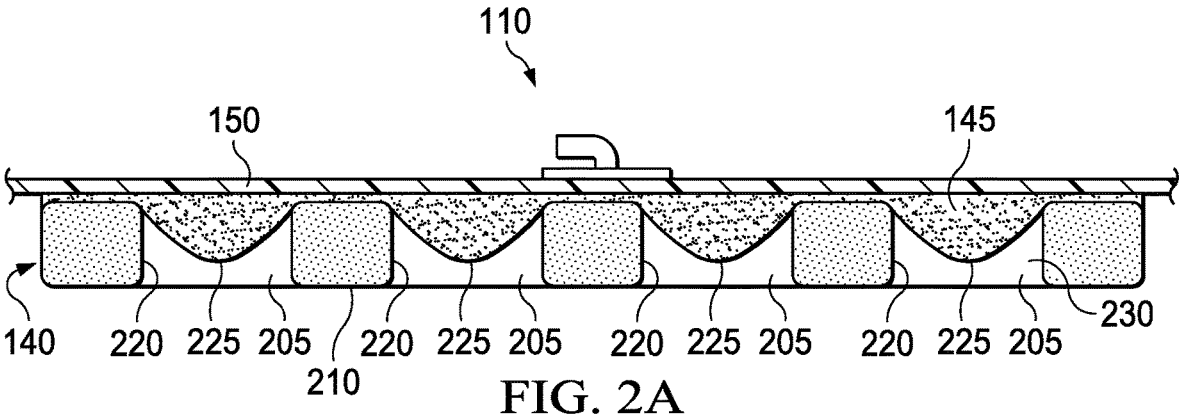
FIGS. 2A-2B are schematic section views of an example of a dressing that may be associated with an example embodiment of the therapy system of FIG. 1.
Figure 2B:
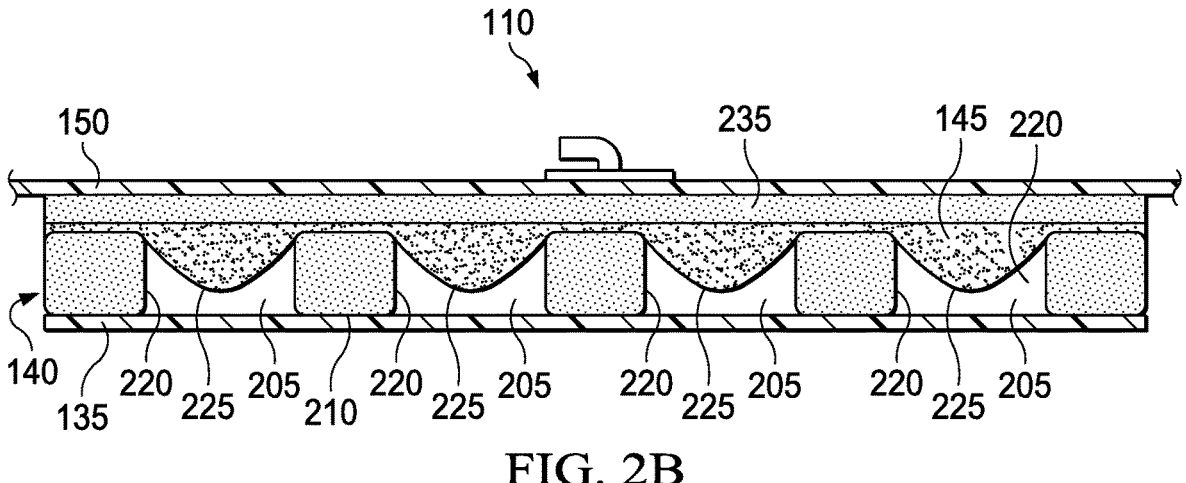

FIGS. 2A-2B are schematic section views of an example of the dressing 110, illustrating additional details that may be associated with some embodiments. FIG. 2A includes an example of the contact layer 140 and an example of the retainer layer 145. In some embodiments, as illustrated in FIG. 2A, the cover layer 150 may be disposed over one or more other layers.

The contact layer 140 can be generally adapted to partially or fully contact a tissue site. The contact layer 140 may take many forms, and may have many sizes, shapes, or thicknesses depending on a variety of factors, such as the type of treatment being implemented or the nature and size of a tissue site. For example, the size and shape of the contact layer 140 may be adapted to the contours of deep and irregular shaped tissue sites. Moreover, any or all of the surfaces of the contact layer 140 may have projections or an uneven, course, or jagged profile that can induce strains and stresses on a tissue site, which can promote granulation at the tissue site.

In some embodiments, the contact layer 140 may be a manifold. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid such as from a source of instillation solution across a tissue site.

In some illustrative embodiments, the pathways of a manifold may be interconnected to improve distribution or collection of fluids across a tissue site. In some illustrative embodiments, a manifold may be a porous material having interconnected cells or pores. For example, cellular foam, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In other embodiments, perforated, closed-cell foam may be suitable. For example, some embodiments of the contact layer 140 may comprise or consist of closed-cell, cross-linked polyolefin foam with holes. In some embodiments, a manifold may additionally or alternatively comprise projections that form interconnected fluid pathways. For example, a manifold may be molded to provide surface projections that define interconnected fluid pathways.

The average cell size of foam may vary according to needs of a prescribed therapy. For example, in some embodiments, the contact layer 140 may be foam having pore sizes in a range of 400-600 microns. The tensile strength of the contact layer 140 may also vary according to needs of a prescribed therapy. For example, the tensile strength of foam may be increased for instillation of topical treatment solutions. In some examples, the contact layer 140 may be reticulated polyurethane foam such as found in GRANUFOAM™ dressing or V.A.C. VERAFLO™ dressing, both available from KCI of San Antonio, Texas.

In some embodiments, the contact layer 140 may be formed from material that is mechanically or chemically compressed to increase density at ambient pressure. For example, the contact layer 140 may comprise or consist of a compressible material, such as a foam that has been compressed. Compressed foam may be characterized by a firmness factor that is defined as a ratio of the density of foam in a compressed state to the density of the same foam in an uncompressed state. In some embodiments, the contact layer 140 may have a firmness factor of about 1 to about 10. For example, compressed foam having a density that is five times greater than a density of the same foam in an uncompressed state may be characterized as having a firmness factor of 5. Increasing the firmness factor of foam may increase a stiffness of the foam in a direction that is parallel to a thickness of the foam. For example, increasing the firmness factor of the contact layer 140 may increase a stiffness of the contact layer 140 in a direction that is parallel to the thickness of the contact layer 140. In some embodiments, the contact layer 140 may comprise or consist of compressed reticulated polyurethane foam, and may have a density of about 0.03 grams per centimeter3 (g/cm3) in its uncompressed state. If the foam is compressed to have a firmness factor of 5, the foam may be compressed until the density of the foam is about 0.15 g/cm3. In some embodiments, the contact layer 140 may comprise or consist of a compressed foam have a thickness between about 4 millimeters to about 15 millimeters, and more specifically, about 8 millimeters at ambient pressure.

Generally, compressed foam exhibits less deformation under negative pressure than a similar uncompressed foam. The decrease in deformation may be caused by the increased stiffness as reflected by the firmness factor. If subjected to the stress of negative pressure, compressed foam may flatten less than uncompressed foam of similar material. In some examples, if the thickness of the contact layer 140 is about 8 millimeters at ambient pressure, the contact layer 140 may have a thickness between about 1 millimeter and about 5 millimeters under therapeutic levels of negative pressure, and, generally, greater than about 3 millimeters. The stiffness of compressed foam in the direction parallel to the thickness of the foam may allow the foam to be more compliant or compressible in other directions, such as directions perpendicular to the thickness.

The contact layer 140 may be either hydrophobic or hydrophilic. In an example in which the contact layer 140 may be hydrophilic, the contact layer 140 may also wick fluid away from a tissue site, while continuing to distribute negative pressure to the tissue site. The wicking properties of the contact layer 140 may draw fluid away from a tissue site by capillary flow or other wicking mechanisms. An example of a hydrophilic foam is a polyvinyl alcohol, open-cell foam such as V.A.C. WHITEFOAM™ dressing available from KCI of San Antonio, Texas. Other hydrophilic foams may include those made from polyether. Other foams that may exhibit hydrophilic characteristics include hydrophobic foams that have been treated or coated to provide hydrophilicity.

The contact layer 140 may further promote granulation at a tissue site when pressure within the sealed therapeutic environment is reduced. For example, any or all of the surfaces of the contact layer 140 may have an uneven, coarse, or jagged profile that can induce microstrains and stresses at a tissue site if negative pressure is applied through the contact layer 140.

In some embodiments, the contact layer 140 may be constructed from resorbable or bioresorbable materials. As used herein, the terms "resorbable" or "bioresorbable" are synonymous and refer to the ability of at least a portion of a material to disintegrate, degrade, or dissolve upon exposure to physiological fluids or processes such that at least a portion of the material may be absorbed or assimilated, for example, at a tissue site or in vivo in a mammalian body. Resorbability or bioresorbability may be exhibited as a result of a chemical process or condition, a physical process or condition, or combinations thereof. Suitable bioresorbable materials may include, without limitation, a polymeric blend of polylactic acid (PLA) and polyglycolic acid (PGA). The polymeric blend may also include without limitation polycarbonates, polyfumarates, and capralactones. The contact layer 140 may further serve as a scaffold for new cell-growth, or a scaffold material may be used in conjunction with the contact layer 140 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the contact layer 140 may be formed from thermoplastic elastomers (TPE), such as styrene ethylene butylene styrene (SEBS) copolymers, or thermoplastic polyurethane (TPU). The contact layer 140 may be formed by combining sheets of TPE or TPU. In some embodiments, the sheets of TPE or TPU may be bonded, welded, adhered, or otherwise coupled to one another. For example, in some embodiments, the sheets of TPE or TPU may be welded using radiant heat, radio-frequency welding, or laser welding. Supracor, Inc., Hexacor, Ltd., Hexcel Corp., and Econocorp, Inc. may produce suitable TPE or TPU sheets for the formation of the contact layer 140. In some embodiments, sheets of TPE or TPU having a thickness between about 0.2 mm and about 2.0 mm may be used to form a structure suitable for the contact layer 140. In some embodiments, the contact layer 140 may be formed from a 3D textile, also referred to as a spacer fabric. Suitable 3D textiles may be produced by Heathcoat Fabrics, Ltd., Baltex, and Mueller Textil Group. The contact layer 140 can also be formed from felted foam, polyurethane, silicone, polyvinyl alcohol, and metals, such as copper, tin, silver or other beneficial metals.

In some embodiments, the contact layer 140 may have a substantially uniform thickness. A thickness between about 5.0 mm to about 20 mm or about 5.0 mm to about 20 mm may be suitable for some configurations. For example, some embodiments of the contact layer 140 may have a thickness of about 8 millimeters. In some embodiments, the thickness may not be strictly uniform. For example, a tolerance of about 2 millimeters may be suitable for some embodiments.

In some embodiments, the contact layer 140 may have one or more holes, cavities, or recesses. In general, the holes 205 may extend through the contact layer 140. For example, in FIG. 2A the contact layer 140 has one or more holes 205, which may extend through the contact layer. A height or depth of between 1 mm to 40 mm and a width of between 1 mm to 30 mm may be suitable for some examples. A depth of about 8 mm may be suitable for some embodiments. As illustrated in FIG. 2A, one or more or all of the holes 205 may be a through-hole that extends through the contact layer 140 from a first surface 210 to a second surface 215. In some examples, the holes 205 may be formed by perforating the contact layer 140 or injection molding. The holes 205 may be formed by walls 220 of the contact layer 140.

In other embodiments, one or more of the holes 205 may be a blind hole or other recess, which does not pass completely through the contact layer 140. For example, one or more of the holes may extend into the contact layer 140 from the first surface 210 and have a depth that is less than the thickness of the contact layer 140.

The holes 205 may be defined by walls 220 in the contact layer 140. In some embodiments, an interior surface of the walls 220 may be generally perpendicular to the first surface 210 and the second surface 215 of the contact layer 140. In still other embodiments, the walls 220 may have a substantially smooth surface between the first surface 210 and the second surface 215 of the contact layer 140. In still other embodiments, the holes 205 may be tapered, and may have conical, pyramidal, or other irregular geometries. In some embodiments, the holes 205 may be formed so that a central axis of each of the holes 205 is orthogonal to the first surface 210, the second surface 215, or both. In other embodiments, one or more of the holes 205 may be formed so that the central axis is oblique to the first surface 210, the second surface 215, or both.

In some embodiments, the retainer layer 145 may have one or more projections, protrusions, nodules, or protuberances. As illustrated in the example of FIG. 2A, the retainer layer 145 may have projections 225 protruding or configured to protrude into one or more of the holes 205 of the contact layer 140. The retainer layer 145 may be made of a foam, such as a reticulated foam. In some examples, the retainer layer 145 may be made of an open-cell foam having relatively larger pore size. An average pore size between about 10 pores per inch (ppi) and about 80 ppi may be suitable for some examples. The retainer layer 145 may be flexible, semi-rigid, or rigid. In some embodiments, the retainer layer 145 may be more flexible or compressible than the contact layer 140. In additional embodiments, the retainer layer 145 may be less dense than the contact layer 140. In certain embodiments, the retainer layer 145 may have a thickness less than the contact layer 140.

In some embodiments, the projections 225 may be formed as an integral portion extending from the retainer layer 145. In other examples, the projections 225 may be coupled to the retainer layer 145. The projections 225 may be made of foam, such as reticulated foam. In some embodiments, the projections 225 may protrude from the retainer layer 145 into the holes 205. In some examples, the depth of the projections 225 is less than the depth of the holes 205. For example, the projections 225 may have a depth of about 6 millimeters (mm) if the holes 205 have a depth of about 8 mm. A depth between about 1 mm and about 30 mm may be suitable for some embodiments. In some embodiments, the projections 225 may have a diameter between about 1 mm and about 30 mm (for example, 10 mm). Additionally or alternatively, the projections 225 may have a shape that is complementary to a shape of the holes 205 in the contact layer 140. In non-limiting exemplary embodiments, the projections 225 may have a shape such as a triangle, trapezoid, ellipse, diamond, rectangle, oval, square, circle, octagon, or other suitable shape.

In some embodiments, the projections 225 may at least partially fill some or all of the holes 205. Alternatively, the projections 225 may substantially fill some or all of the holes 205. For example, at least some of the projections 225 can have a tapered end disposed within the holes 205. In some embodiments, there may be a space 230 between the projections 225 and the contact layer 140. In some examples, the projections 225 may have an even or uneven outer surface, such as a ragged outer surface.

In some embodiments, the cover layer 150 may be disposed adjacent to the retainer layer 145, as illustrated in the example of FIG. 2A. The cover layer 150 may provide a bacterial barrier and protection from physical trauma. In some embodiments, the cover layer 150 may also be constructed from a material that can reduce evaporative losses and provide a fluid seal between two components or two environments, such as between a therapeutic environment and a local external environment. The cover layer 150 may be, for example, an elastomeric film or membrane that can provide a seal adequate to maintain a negative pressure at a tissue site for a given negative-pressure source. The cover layer 150 may have a high moisture-vapor transmission rate (MVTR) in some applications. For example, the MVTR may be at least 300 g/m2 per twenty-four hours in some embodiments. In some example embodiments, the cover layer 150 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

In some embodiments, the contact layer 140 and the retainer layer 145 may be integrated into one component or an integral layer, and may be inseparable. For example, the retainer layer 145 may be laminated to the contact layer 140 in some embodiments.

In some embodiments, additional layers or components may be present in the dressing. For example, at least one further layer or component may be present between the contact layer 140 and the debriding matrix 135, at least one further layer or component may be present adjacent to a surface of the debriding matrix 135 opposed to a surface of the debriding matrix 135 adjacent to the contact layer 140, and/or at least one further layer or component may be present adjacent to a surface of the contact layer 140 opposed to a surface of contact layer 140 adjacent to the debriding matrix 135.

FIG. 2B is a schematic view of another example of the dressing 110 in which the cover layer 150 is not directly coupled to the retainer layer 145. As shown in FIG. 2B, a filler layer 235 may be optionally disposed between the retainer layer 145 and the cover layer 150. For example, the filler layer 235 may be disposed adjacent to the retainer layer 145 to increase the depth of the dressing 110. Also as illustrated in FIG. 2B, the debriding matrix 135 can be optionally disposed adjacent to or adhered to a surface of the contact layer 140 in some embodiments. For example, the debriding matrix 135 may be in the form of a continuous or non-continuous coating, film, gel, layer and/or sheeting, which may be adhered, fixed, fastened, or joined on the contact layer 140. In some embodiments, the debriding matrix 135 may be a coating on at least a portion of a surface of the contact layer 140, for example, the debriding matrix 135 may be coated on at least about 10%, at least about 25%, at least about 50%, at least about 75% or at least about 95% of a surface of the contact layer 140. In some embodiments, the debriding matrix 135 may be a coating on substantially an entire surface of the contact layer 140, for example, the debriding matrix 135 may be coated on at least about 99%, 99.9% or about 100% of a surface of the contact layer 140.

In some embodiments, the debriding matrix 135 may only cover a portion of the holes 205, thus at least a portion of the holes 205 may not be covered by the debriding matrix 135. In other embodiments, the debriding matrix 135 may be a solid sheet, covering the holes 205 as illustrated in the example of FIG. 2B. In other embodiments, the debriding matrix 135 may at least partially fill at least a portion of the holes 205 or at least partially fill substantially all of the holes 205. Alternatively, the debriding matrix 135 may substantially fill at least a portion of the holes 205 or substantially fill substantially all of the holes 205. In some embodiments, the debriding matrix 135 may be at least partially removable or separable from the contact layer 140. For example, the debriding matrix 135 can be removed from the contact layer 140 and applied directly to a tissue site.

The thickness of the debriding matrix 135 may vary. A thickness in a range of about 1.0 mm to about 10 mm, about 1.0 mm to about 5.0 mm, or about 1.0 mm to about 3.0 mm may be suitable for some embodiments. In some embodiments, the debriding matrix 135 may be porous, or may have holes, slits, fenestrations, fluid pathways or other means for fluid flow through the debriding matrix 135.

In various embodiments, the debriding matrix 135 may comprise at least one debriding agent and a polymer. In some embodiments, the debriding matrix 135 may have a pH of about 2 to about 10 or a lower pH, for example, a pH of about 1.0 to about 6.0 a pH of about 2.0 to about 5.0, or a pH of about 2.5 to about 4.0, wherein a lower pH may further aid in wound healing. The debriding agent may be any enzyme capable of debriding a tissue site or wound. As used herein, the term "debriding" or "debridement" refers to the softening, weakening, removal, detachment and/or disruption of tissue and/or cells, such as necrotic tissue, biofilm, slough, eschar, and other debris from a tissue site, for example a wound, which can promote healing and/or reduce risk of infection. In some embodiments, the debriding agent advantageously may be active (i.e., causing debridement or disruption of tissue) across a broad pH range, for example, a pH of about 2 to about 12, or about 2 to about 10, for example, within a tissue site or wound. The debriding agent may be present in varying concentrations and/or United States Pharmacopeia units (USP units) of activity, for example, about 0.25 USP units to about 1,000 USP units, about 0.25 USP units to about 500 USP units, about 0.25 USP units to about 300 USP units or about 30 USP units to about 300 USP units. In some embodiments, the debriding agent may present in advantageously higher concentrations and/or USP units of activity for enhanced debridement. In some embodiments, the debriding agent may be selected from the group consisting of papain, urea, streptokinase, streptodornase, trypsin, collagenase, fibrinolysin, deoxyribonuclease (DNase), fibrinolysin with DNase (fibrinolysin/DNase), bromelain, and a combination thereof.

The polymer may be any suitable organic polymer for immobilizing the debriding agent therein. Additionally, the polymer may be biodegradable. As used herein, the term "biodegradable" refers to a material that is capable of chemically and/or physically deteriorating or breaking down, for example, upon exposure to a tissue site and/or physiological fluids or processes. "Biodegrading" includes tearing, breaking, severing, fracturing, dissolving, dissociating, and the like. Terms such as "soluble," "dissolvable," "dissociable," "tearable," "breakable," "severable," "fracturable," "disruptable" and the like, may be used and refer to materials that are capable of biodegrading. Biodegrading may be exhibited as a result of a chemical process or condition, a physical process or condition, or combinations thereof. Examples of suitable polymers include, but are not limited to polysaccharides (e.g., citrus fruit pectin, starches, fecula, agar), proteins (e.g., collagen, gelatin, albumin), vegetable gums (e.g., xantham gum, locust bean, guar), and combinations thereof. Additionally or alternatively, the polymer may be bioresorbable.

Depending on desired solubility during use, for example, during instillation cycles, the polymer may have a soluble solid composition of at least about 10%, for example, from about 10% to about 90% or 10% to about 70%. For example, at least about 10% of the polymer may be soluble in an aqueous solution, for example, having a pH of about 2 to about 10. The polymer and/or the debriding matrix 135 may be capable of biodegrading or dissolving during use, for example, when contacted with a tissue site to release the debriding agent, which may debride the tissue site. Complete biodegrading or dissolving of the polymer is not necessary for debriding of the tissue site to occur. Rather, debriding of the tissue site may occur during one of more of the following: when the debriding matrix 135 initially contacts a tissue site; while the polymer biodegrades or dissolves; once the polymer ceases biodegrading or dissolving; and after the polymer has substantially biodegraded or dissolved. Following biodegrading or dissolving of the polymer, release of the debriding agent and/or debriding of the tissue site, the debriding agent and any remaining polymer can be advantageously washed away, for example during instillation therapy at desired time intervals, along with any wound debris. In some embodiments, the polymer and/or the debriding matrix 135 may dissolve at varying rates, for example, as quickly or as slowly as desired. For example, the polymer and/or the debriding matrix 135 may dissolve in a matter of minutes (e.g., 1, 2, 3, 4, 5 minutes, etc.), for example during one therapy cycle, or the polymer and/or the debriding matrix 135 may dissolve over the course of one or more days, for example until an endpoint in therapy.

In some embodiments, the debriding matrix 135 may further comprise one or more of a drying agent, a thickening agent, and slow release agent in varying amounts. Examples of suitable drying agents include, but are not limited to silica gel (e.g., silica xerogel, silica gel fibers), magnesium aluminum silicate, calcium oxide, calcium sulfate, a sulfonate, and combinations thereof. Examples of suitable thickening agents include, but are not limited to glycerol, glycerin, a carbomer, polyethylene glycol and combinations thereof. Without being bound by theory, it is believed that drying and/or thickening agents can aid in disrupting, removing or detaching wound debris by exerting a superficial desiccating and/or denaturing action. Such desiccating and/or denaturing activity along with mechanical action of the dressing can exhibit co-action or synergy in disrupting, removing or detaching wound debris.

In other embodiments, the debriding matrix 135 may further comprise oxidized cellulose. The term "oxidized cellulose" refers to any material produced by the oxidation of cellulose, for example with dinitrogen tetroxide. Such oxidation converts primary alcohol groups on the saccharide residues to carboxylic acid groups, forming uronic acid residues within the cellulose chain. The oxidation generally does not proceed with complete selectivity, and as a result hydroxyl groups on carbons 2 and 3 are occasionally converted to the keto form. These keto units introduce an alkali-labile link, which at pH 7 or higher initiates the decomposition of the polymer via formation of a lactone and sugar ring cleavage. As a result, oxidized cellulose is biodegradable and resorbable or bioresorbable under physiological conditions. In some embodiments, oxidized cellulose present in the debriding matrix 135 may be oxidized regenerated cellulose (ORC), which may be prepared by oxidation of a regenerated cellulose, such as rayon. It has been known that ORC has haemostatic properties. ORC has been available as a haemostatic fabric called SURGICEL® (Johnson & Johnson Medical, Inc.) since 1950. This product may be produced by the oxidation of a knitted rayon material. In some embodiments, the debriding matrix 135 may be operatively coupled to the contact layer 140.

Figure 3:
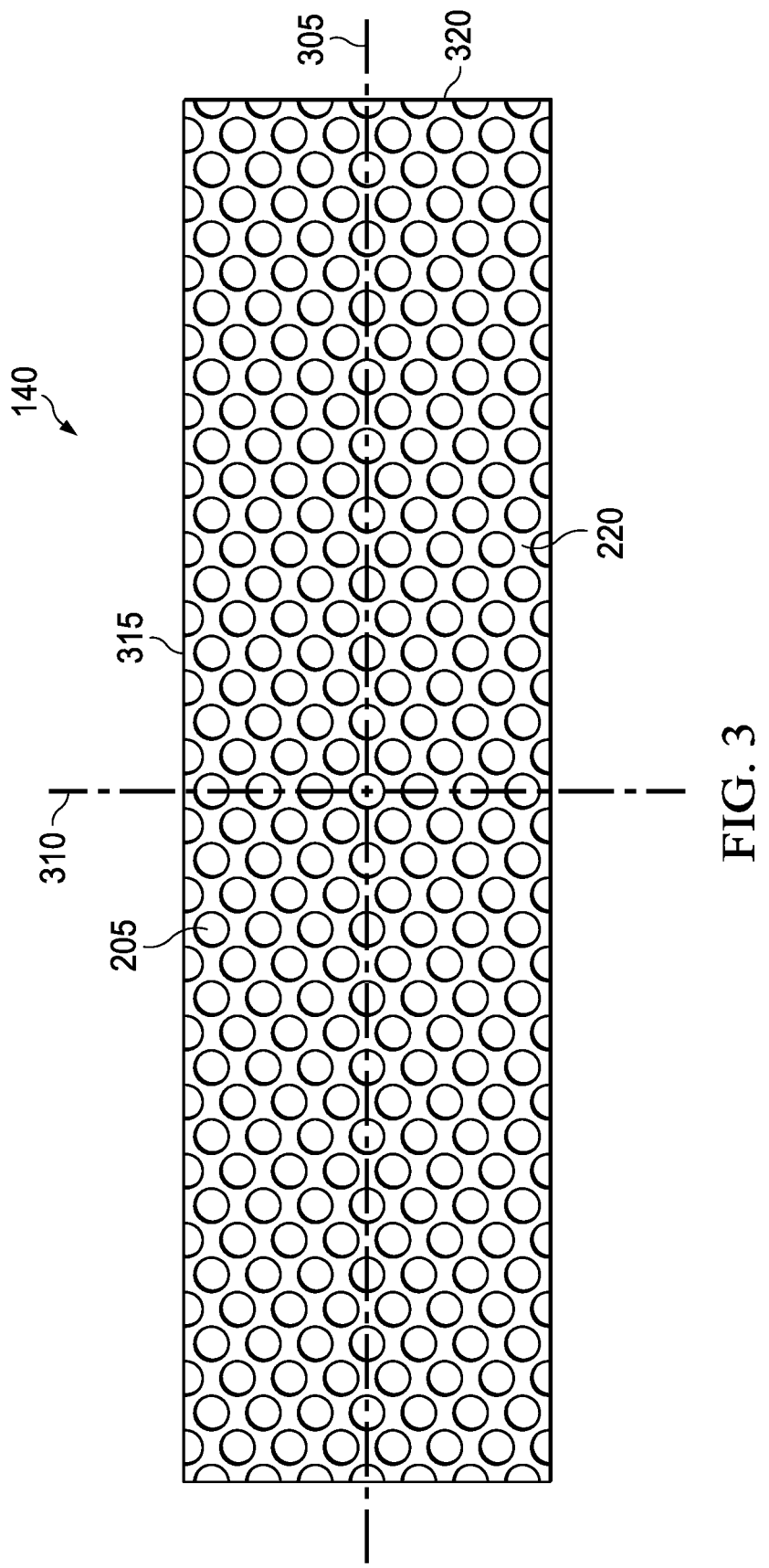
FIG. 3 is a plan view of an example of a contact layer that may be associated with some embodiments of a dressing.

FIG. 3 is a plan view of an example of the contact layer 140, illustrating additional details that may be associated with some embodiments. For example, some embodiments of the holes 205 may have a circular cross-section as illustrated in FIG. 3. In some embodiments, the holes 205 may have an average diameter of greater than about 2.0 mm, greater than about 4.0 mm, greater than about 6.0 mm, greater than about 10 mm or an average diameter between about 5 mm and about 20 mm, and in some embodiments, the average diameter of the holes 205 may be about 10 mm, or in the range of about 5 mm to about 15 mm.

In some embodiments, the contact layer 140 may have a first orientation line 305 and a second orientation line 310 that is perpendicular to the first orientation line 305. The first orientation line 305 and the second orientation line 310 may be lines of symmetry through the contact layer 140. In the example of FIG. 3, the contact layer 140 has a generally rectangular shape with longitudinal edges 315 and latitudinal edges 320. In some embodiments, the first orientation line 305 may be parallel to the longitudinal edges 315.

In some embodiments, the longitudinal edges 315 and the latitudinal edges 320 of the contact layer 140 may not be straight edges. For example, one or more of the holes 205 may overlap the longitudinal edges 315 or the latitudinal edges 320, causing the edge to have a non-linear profile, which may reduce the disruption of keratinocyte migration and enhance re-epithelialization while negative pressure is applied to the dressing 110.

The contact layer 140 may also have a variety of other suitable shapes. For example, the contact layer 140 may have a diamond, square, or circular shape. In some embodiments, the shape of the contact layer 140 may be selected to accommodate the shape or type of a tissue site. For example, the contact layer 140 may have an oval or circular shape to accommodate an oval or circular tissue site.

Figure 4:
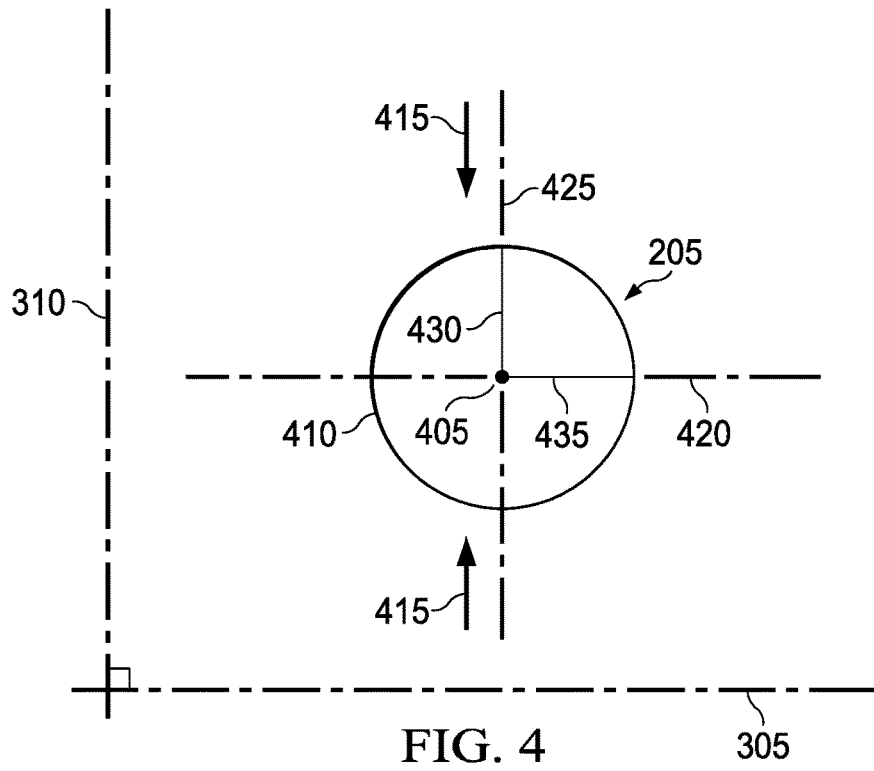
FIG. 4 is a detail view of the contact layer of FIG. 3, illustrating additional details that may be associated with some embodiments.

FIG. 4 is a detail view of one of the holes 205 of FIG. 3, illustrating additional details that may be associated with some embodiments. As illustrated in the example of FIG. 4, one or more of the holes 205 may include a center 405 and a perimeter 410. Each of the holes 205 may also be characterized by a shape factor. The shape factor may represent an orientation of each of the holes 205 relative to the first orientation line 305 and the second orientation line 310. Generally, the shape factor is a ratio of ½ a maximum dimension that is parallel to the desired direction of contraction to ½ a maximum dimension that is perpendicular to the desired direction of contraction. For example, the desired direction of contraction in FIG. 4 may be parallel to the second orientation line 310, as indicated by vector 415 as the direction of a lateral force. A first axis 420 may pass through the center 405 parallel to the first orientation line 305, and a second axis 425 may extend through the center 405 parallel to the second orientation line 310. The shape factor of each of the holes 205 may be defined as a ratio of a first line segment 430 on the second axis 425 extending from the center 405 to the perimeter 410, to a second line segment 435 on the first axis 420 extending from the center 405 to the perimeter 410. For example, if a length of the first line segment 430 is 2.5 mm and the length of the second line segment 435 is 2.5 mm, the shape factor would be 1. In other embodiments, the holes 205 may have other shapes and orientations, for example, oval, hexagonal, elliptical, circular, square, triangular, conical, or amorphous or irregular or a combination thereof and be oriented relative to the first orientation line 305 and the second orientation line 310 so that the shape factor may range from about 0.5 to about 1.10.

Figure 5:
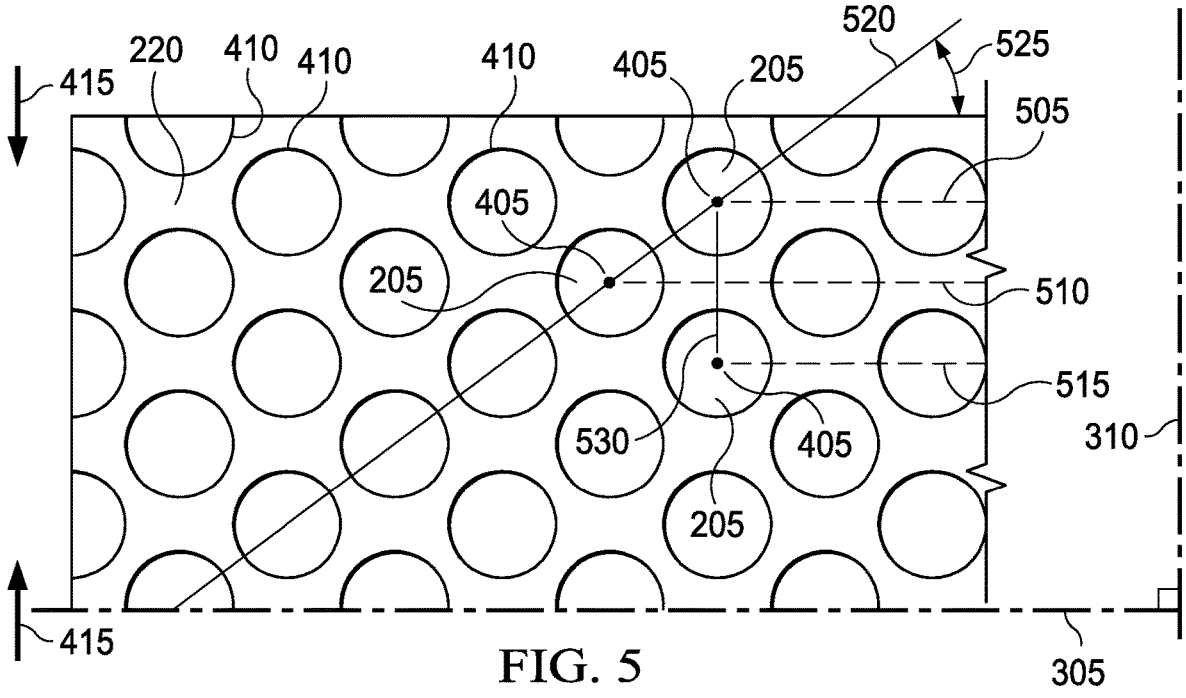
FIG. 5 is another detail view of a portion of the contact layer of FIG. 3, illustrating additional details that may be associated with some embodiments.

FIG. 5 is a detail view of a portion of the holes 205 of FIG. 3, illustrating additional details that may be associated with some embodiments. In some embodiments, the holes 205 may be aligned in parallel rows, for example two or more parallel rows, to form an array, as illustrated in the example of FIG. 5. For example, an array of the holes 205 may include a first row 505, a second row 510, and a third row 515. In some embodiments, a width of the walls 220 between the perimeter 410 of two or more of the holes 205 in a row, such as the first row 505, may be about 5 millimeters. The center 405 of each of the holes 205 in adjacent rows, for example, the first row 505 and the second row 510, may be characterized as being offset along the first orientation line 305. In some embodiments, a strut line 520 passing through the center 405 of each of the holes 205 in adjacent rows may define a strut angle 525 with the first orientation line 305. In some embodiments, the strut angle 525 may be less than about 90°. In other embodiments, the strut angle 525 may be between about 30° and about 70°. In other embodiments, the strut angle 525 may be about 66°. Generally, as the strut angle 525 decreases, a stiffness of the contact layer 140 in a direction parallel to the first orientation line 305 may increase. Increasing the stiffness of the contact layer 140 parallel to the first orientation line 305 may increase the compressibility of the contact layer 140 perpendicular to the first orientation line 305.

In some embodiments, the center 405 of each of the holes 205 in alternating rows may be spaced apart parallel to the second orientation line 310 by a length 530. In some embodiments, the length 530 may be greater than an effective diameter of the holes 205. In some embodiments, the length 530 may be between about 7 mm and about 25 mm.

The contact layer 140 may additionally or alternatively be characterized by a void-space percentage, which reflects a ratio of the void space in the first surface 210 created by the holes 205 to the area defined by the perimeter of the contact layer 140 as shown in FIG. 1. In general, the void-space percentage can be designed to achieve a desirable balance between handling characteristics and flexibility. For example, increasing the void-space percentage may increase the contraction characteristics of the holes 205, and may also decrease the handling characteristics of the contact layer 140. A void-space percentage between about 40% and about 75% may be suitable for some embodiments. For example, some embodiments may have a void-space percentage of about 55%.

In some embodiments, the holes 205 may have an effective diameter between about 3 millimeters and about 20 millimeters. An effective diameter of a non-circular area is a diameter of a circular area having the same surface area as the non-circular area. In some embodiments, one or more of the holes 205 have a non-circular cross-section with an effective diameter of about 3.5 mm. In other embodiments, the holes 205 may have an effective diameter between about 5 mm and about 20 mm.

Generally, the holes 205 are not formed by a foaming process, and can be distinguished from pores or cells of material forming the contact layer 140. For example, a single pore or cell of the material is generally not large enough to extend completely through the contact layer 140. An effective diameter of the holes 205 may be an order of magnitude larger than the effective diameter of the pores or cells of a material forming the contact layer 140. In some embodiments, the effective diameter of the holes may be larger than about 1 mm, while the material of the contact layer 140 may be foam having a pore size less than about 600 microns.

In some embodiments, the holes 205 may be formed during molding of the contact layer 140. In other embodiments, the holes 205 may be formed by cutting, melting, drilling, or vaporizing the contact layer 140 after the contact layer 140 is formed. For example, a through-hole may be formed by reaming, drilling, or milling a hole completely through the contact layer 140. Additionally or alternatively, the holes 205 may be laser-cut into the contact layer 140.

In some embodiments, formation of the holes 205 may thermoform the material of the contact layer 140, causing the interior surface of the holes 205 to be non-porous. For example, laser-cutting the holes 205 into the contact layer 140 may plastically deform the material of the contact layer 140, closing any pores on the interior surfaces of the holes 205. Alternatively or additionally, a smooth interior surface of the holes 205 may be formed by a applying or coating a smooth material to the holes 205. In some embodiments, a smooth interior surface may limit or otherwise inhibit ingrowth of tissue into the contact layer 140 through the holes 205.

Figure 6:
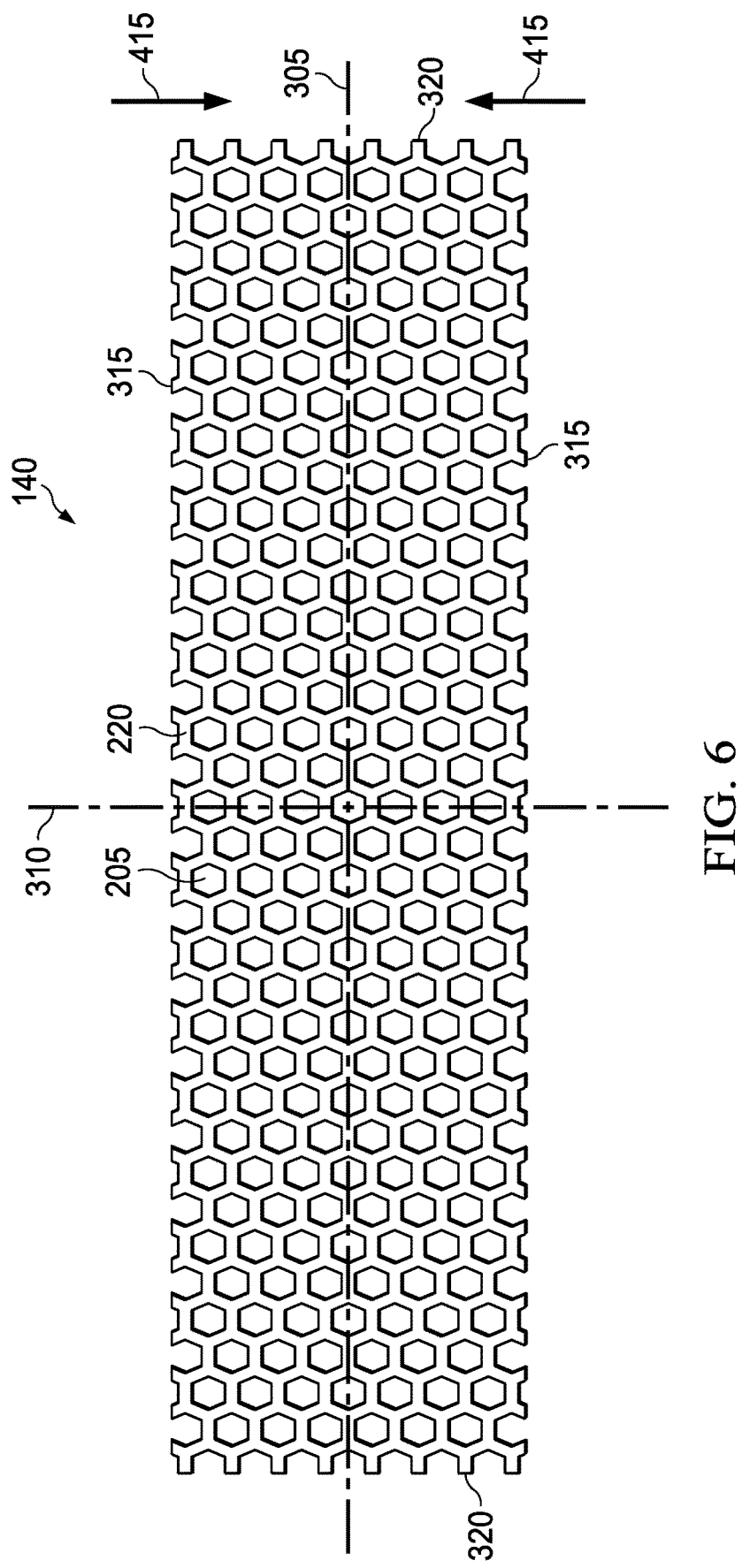
FIG. 6 is a plan view of another example of a contact layer, illustrating additional details that may be associated with some embodiments.
Figure 7:
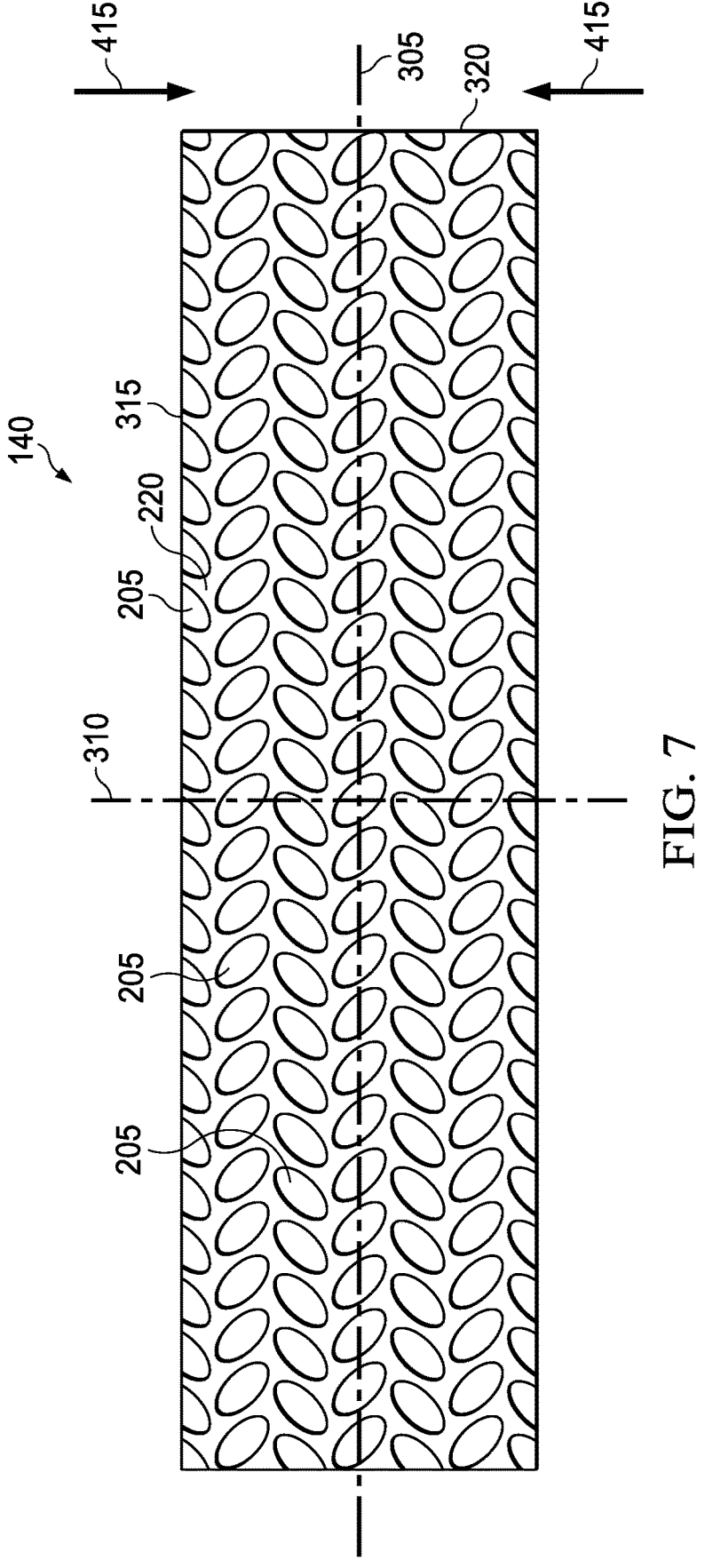
FIG. 7 is a plan view of another example of a contact layer, illustrating additional details that may be associated with some embodiments.
Figure 8:
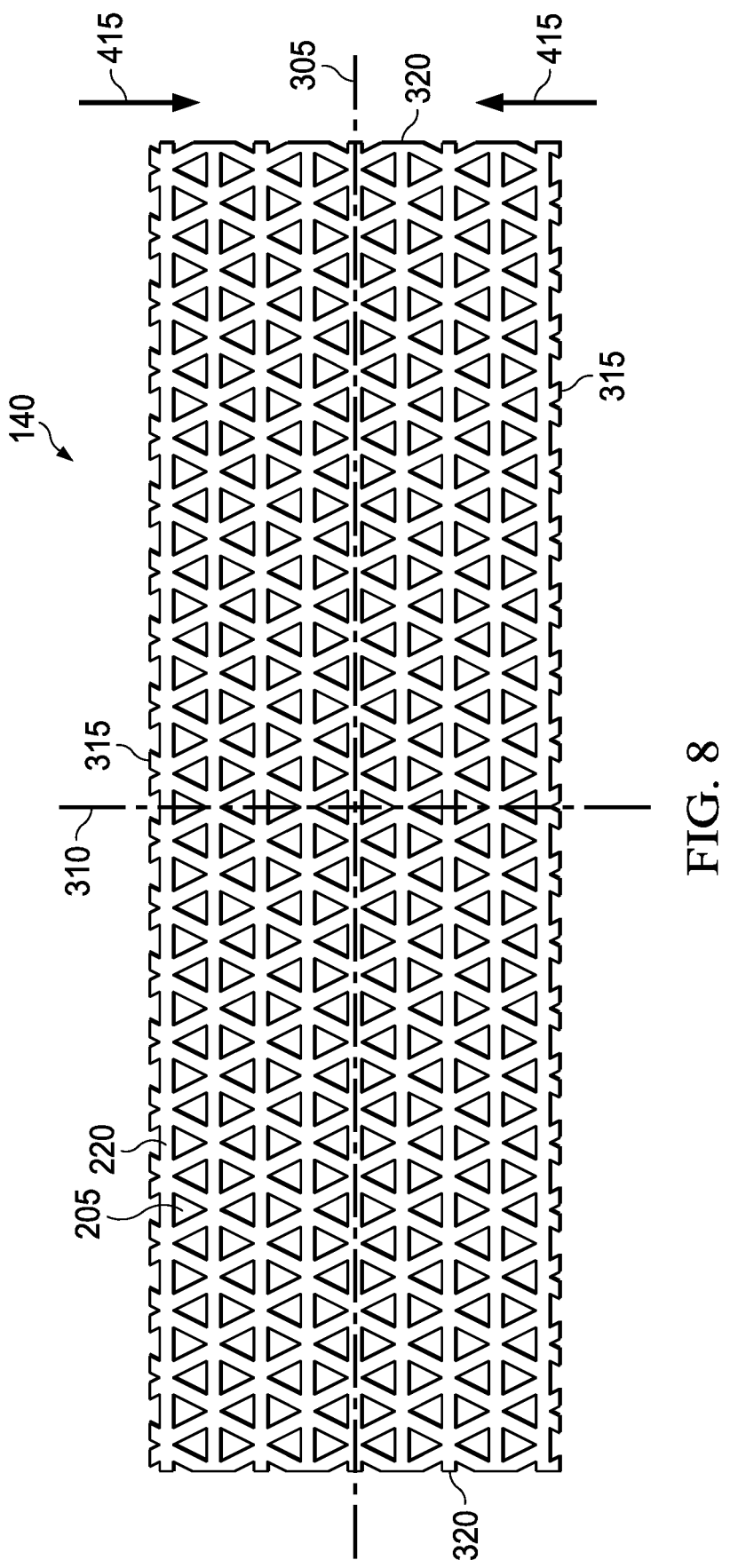
FIG. 8 is a plan view of another example of a contact layer, illustrating additional details that may be associated with some embodiments.

The shape of the holes 205 may vary in different embodiments of the contact layer 140 to vary the concentration of stresses. For example, FIG. 6 is a plan view of another embodiment of the contact layer 140, illustrating additional details in which the holes 205 have a hexagonal cross-section, which can cause a lateral force 415. FIG. 7 is a plan view of another example of the contact layer 140, illustrating additional details in which the holes 205 have an elliptical or oval cross-section and a lateral force 415. FIG. 8 is a plan view of another example of the contact layer 140, illustrating additional details in which the holes 205 have a triangular cross-section and a lateral force 415.

B. Negative-Pressure Supply

A negative-pressure supply, such as the negative-pressure source 105, may be a reservoir of air at a negative pressure, or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

C. Container

The container 115 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

D. Controller

A controller, such as the controller 120, may be a microprocessor or computer programmed to operate one or more components of the therapy system 100, such as the negative-pressure source 105. In some embodiments, for example, the controller 120 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the contact layer 140, for example. The controller 120 may be configured to receive one or more input signals, such as a feedback signal, and programmed to modify one or more operating parameters based on the input signals.

E. Sensors

Sensors, such as the first sensor 125 or the second sensor 130, are generally known in the art as any apparatus operable to detect or measure a physical phenomenon or property, and generally provide a signal indicative of the phenomenon or property that is detected or measured. For example, the first sensor 125 and the second sensor 130 may be configured to measure one or more operating parameters of the therapy system 100. In some embodiments, the first sensor 125 may be a transducer configured to measure pressure in a pneumatic pathway and convert the measurement to a signal indicative of the pressure measured. In some embodiments, for example, the first sensor 125 may be a piezoresistive strain gauge. The second sensor 130 may optionally measure operating parameters of the negative-pressure source 105, such as the voltage or current, in some embodiments. Preferably, the signals from the first sensor 125 and the second sensor 130 are suitable as an input signal to the controller 120, but some signal conditioning may be appropriate in some embodiments. For example, the signal may need to be filtered or amplified before it can be processed by the controller 120. Typically, the signal is an electrical signal, but may be represented in other forms, such as an optical signal.

F. Attachment Device

An attachment device may be used to attach the cover layer 150 to an attachment surface, such as undamaged epidermis, a gasket, or another cover. The attachment device may take many forms. For example, an attachment device may be a medically-acceptable, pressure-sensitive adhesive configured to the cover layer 150 to epidermis around a tissue site. In some embodiments, for example, the cover layer 150 may be coated with an adhesive, such as an acrylic adhesive, which may have a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

G. Solution Source

The solution source 165 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

II. Methods of Use

In some embodiments, the dressing 110 and the therapy system 100 can be used to provide negative-pressure treatment and debridement of tissue to aid in tissue healing. In some embodiments, a method for debriding a tissue site may comprise positioning a dressing, such as the dressing 110, adjacent to a tissue site. In some examples, the contact layer 140 may be positioned on or over the tissue site. In other examples having the debriding matrix 135, the debriding matrix may be positioned on the tissue site. The debriding matrix 135 and the contact layer 140 may be positioned separately or together, such that the debriding matrix 135 may be adjacent to the tissue site and the contact layer 140 may be adjacent to the debriding matrix. For example, a separate debriding matrix or a debriding matrix which has been separated from a contact layer may be positioned adjacent to the tissue site, followed by positioning of the contact layer adjacent to the debriding matrix. Alternatively, the dressing 110 with the debriding matrix 135 operatively coupled to the contact layer 140 may be positioned adjacent to the tissue site.

Negative pressure may be supplied to the dressing 110 for treatment of the tissue site. In some embodiments, negative pressure may be delivered to the tissue site through the contact layer 140 or through the contact layer 140 and the debriding matrix 135. For example, the debriding matrix 135 may be porous, or may have holes, slits, fenestrations or other fluid pathways through which fluid may be delivered to the tissue site. Additionally or alternatively, the debriding matrix 135 may be at least partially biodegraded or dissolved by one or more of exudate, instillation solution, and negative pressure, which can create fluid pathways. At least a portion of debriding matrix 135 may biodegrade or dissolve and continue to biodegrade or dissolve throughout treatment. In some embodiments, substantially all of the debriding matrix may biodegrade or dissolve during treatment. One or more debriding agents may contact the tissue site and advantageously debride, for example, through enzymatic debridement, at least a portion of the tissue site including debris present therein. In some embodiments, debridement may only comprise enzymatic debridement.

Advantageously, time between dressing changes can be increased, for example, by controlling the rate at which the debriding matrix 135 biodegrades or dissolves. For example, the dressing may remain adjacent to a tissue site for greater than 1 day, greater than 3, greater than 5 days, or greater than 7 days, before a dressing change. In some embodiments, the dressing may remain adjacent to a tissue for about 1 to 7 days or about 3 to 5 days. Further, use of instillation therapy during these intervals between dressing changes can advantageously remove at least a portion of a debriding agent from the tissue site so that toxicity to the tissue site can be minimized.

Figures 9A, 9B:
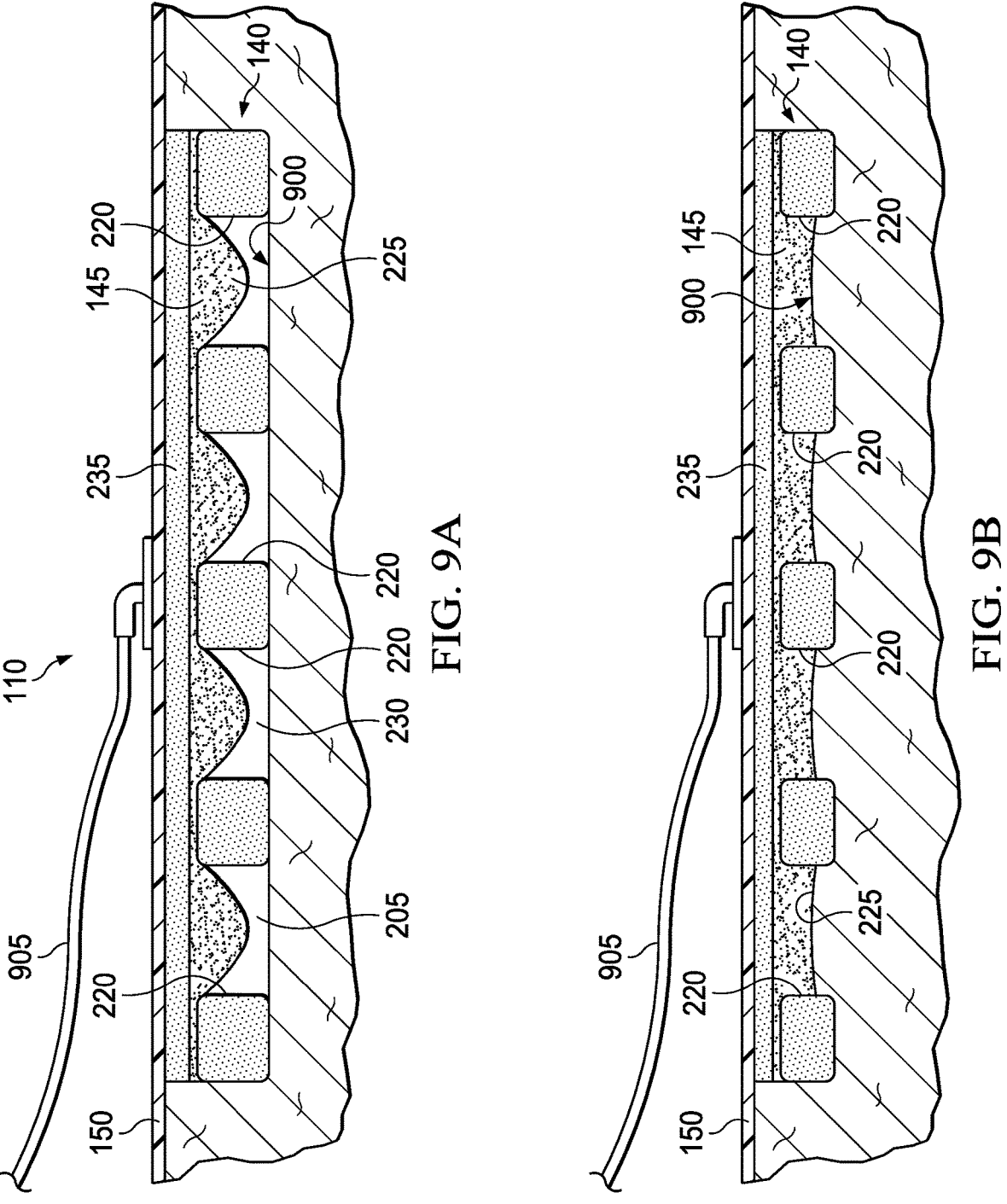
FIG. 9A is a schematic view of the example dressing of FIG. 2A applied to a tissue site.
FIG. 9B is a schematic view of the dressing of FIG. 10A under negative pressure.

FIG. 9A is a schematic view of the dressing 110 of FIG. 2A, illustrating additional details that may be associated with some embodiments of using the dressing 110 to treat a tissue site 900. In some examples, the tissue site 900 may include debris. For example, the debris may comprise one or more of biofilms, necrotic tissue, lacerated tissue, devitalized tissue, contaminated tissue, damaged tissue, infected tissue, exudate, highly viscous exudate, and fibrinous slough. The debris may cover all or a portion of the tissue site.

If not removed, the debris may inhibit the efficacy of tissue treatment and slow the healing of the tissue site. For example, biofilms can comprise a microbial infection that can cover the tissue site and impair healing of the tissue site. Biofilms can also lower the effectiveness of topical antibacterial treatments by preventing the topical treatments from reaching the tissue site.

Necrotic tissue may be dead tissue resulting from infection, toxins, or trauma that caused the tissue to die faster than the tissue can be removed by the normal body processes that regulate the removal of dead tissue. Sometimes, necrotic tissue may be in the form of slough, which may include viscous liquid mass of tissue. Generally, slough is produced by bacterial and fungal infections that stimulate an inflammatory response in the tissue. Slough may be a creamy yellow color and may also be referred to as pus. Necrotic tissue may also include eschar. Eschar may be a portion of necrotic tissue that has become dehydrated and hardened. Eschar may be the result of a burn injury, gangrene, ulcers, fungal infections, spider bites, or anthrax, and can be difficult to remove.

In use, the dressing 110 may be placed in or on a tissue site, and the cover layer 150 may be sealed to an attachment surface, such as epidermis peripheral to a tissue site. The geometry and dimensions of the retainer layer 145, the filler layer 235, or the cover layer 150 may vary to suit a particular application or anatomy. For example, the geometry or dimensions of the cover layer 150 may be adapted to provide an effective and reliable seal at or around a tissue site. Additionally or alternatively, the dimensions may be modified to increase the surface area for the dressing 110 to enhance the movement and proliferation of epithelial cells at or around a tissue site and reduce the likelihood of granulation tissue in-growth. In some embodiments, the dressing 110 optionally may be customized prior to positioning adjacent to the tissue site. Customizing may include cutting and/or sizing the dressing 110 as needed for use with the tissue site. For example, the contact layer 140 and the retaining layer 145 may be customized either separately or together as needed and then positioned on the tissue site. In some embodiments, the filler layer 235 optionally may be positioned over or adjacent to the retainer layer 145 such that the filler layer 235 may be disposed between the cover layer 150 and the retainer layer 145.

A negative-pressure source can be fluidly coupled to a sealed environment through the cover layer 150 and the tissue site. For example, a fluid conductor 905 may have a first end coupled to the filler layer 235 or the retainer layer 145 and a second end coupled to the negative-pressure source 105. The negative-pressure source can reduce the pressure in the sealed environment. In some embodiments, negative pressure may be supplied to the sealed environment until the pressure in the sealed environment reaches a predetermined therapy pressure. Negative pressure may be supplied to the sealed environment for any suitable amount of time, for example, at least about 10 minutes, at least about 30 minutes or less than about 60 minutes. In other embodiments, the therapy period may be longer or shorter as needed to supply appropriate negative-pressure therapy to a tissue site.

FIG. 9B illustrates the dressing 110 of FIG. 9A with negative pressure applied. As illustrated in the example of FIG. 9B, the contact layer 140 can contract under negative pressure. In some examples, the space 230 may decrease or be eliminated, and slough or other tissue can be drawn into the holes 205. In some examples, the contact layer 140 may be configured to substantially retain its shape under negative pressure, which can encourage tissue to be drawn into the holes or recesses. For example, the contact layer 140 may have a density or a thickness greater than that of the retainer layer 145. In FIG. 9B, portions of the tissue site 900 are drawn into contact with the projections 225, which can debride or remove the slough or other tissues in the holes 205 of the contact layer 140.

Additionally or alternatively, the retainer layer 145, the projections 225, or both may be drawn down under negative pressure. For example, the projections 225 may be drawn into contact with tissue drawn up through the holes 205 in some embodiments of the contact layer 140. The projections 225 may be formed to a predetermined size, a predetermined shape, or a predetermined firmness factor, which can depend on prescribed treatment factors. For example, treatment factors may include uniformity or aggressiveness of contact with tissue. In some examples, the size of the projections 225 may be selected based on the firmness factor and shape of the projections 225, magnitude of negative pressure in the sealed environment, the dimensions of the holes 205, the firmness factor of the retainer layer 145, and the shape and size of the tissue drawn into the holes 205 to provide a debriding force for the tissue drawn into the holes 205. In some embodiments, the projections 225 may have a depth, size, shape, and thickness selected to create a debriding force applied to tissues drawn into the holes 205 under a negative pressure. The firmness factor of the projections 225 and the retainer layer 145 can be selected to control the depth of the projections 225 into the holes 205 under a negative pressure. In some embodiments, the projections 225 may have a firmness factor equal to or less than that of the contact layer 140.

As illustrated in FIG. 9B, the projection 225 may be configured to be exposed to the tissue or nodules inside the holes 205 and may be used as a cutting edge to disrupt the tissue or nodules when under negative pressure. The projection 225 may contact at least a portion of the outer surface of the holes 205 to debride in the negative pressure therapy.

If the dressing 110 is under negative pressure, some portions of the large pores of the retainer layer 145, especially of the projections 225, may be compressed against the macro-deformation of a tissue site, such as a wound bed. If the negative pressure is held on a tissue site, the large pores of the retainer layer 145 may accept slough and allow macro-deformation to form. The large pore size of the retainer layer 145 may also help apply micro-strain to the top portions of the macro-deformation on a tissue site.

Following the therapy period, the therapy system 100 may vent the environment. For example, the therapy system 100 may fluidly couple the sealed environment to the atmosphere, allowing the sealed environment to return to ambient pressure. In some embodiments, the therapy system 100 may vent the sealed environment for about 1 minute, for example, by maintaining the sealed environment at ambient pressure. In other embodiments, the therapy system 100 may vent the sealed environment for longer or shorter periods. After venting the sealed environment, the negative-pressure source 105 may begin another negative-pressure therapy cycle. In some embodiments, negative pressure may be supplied to the sealed environment for about 1 minute and the sealed environment may be vented for about 1 minute.

In some embodiments, negative-pressure treatment may be provided cyclically, alternately applying and venting negative pressure in the sealed environment, for example, via the therapy system 100.

Figure 10:
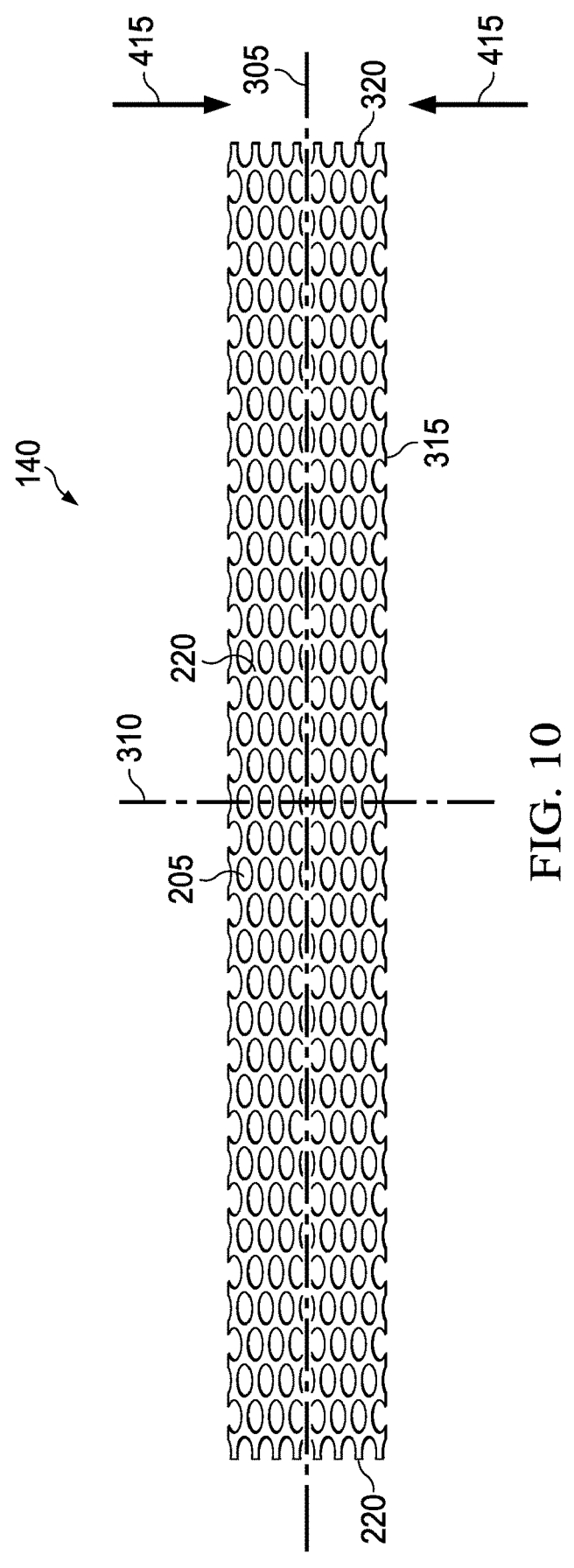

FIG. 10 is a view of the contact layer 140 contracting under negative pressure, illustrating additional details that may be associated some embodiments of the dressing 110. As shown in FIG. 10, the first orientation line 305 and the second orientation line 310 may be used to orient the desired directions of contraction of the contact layer 140. For example, the desired direction of contraction may be parallel to the second orientation line 310 and perpendicular to the first orientation line 305. In other embodiments, the desired direction of contraction may be parallel to the first orientation line 305 and perpendicular to the second orientation line 310. In still other embodiments, the desired direction of contraction may be at an oblique angle to both the first orientation line 305 and the second orientation line 310. In other embodiments, the contact layer 140 may not have a desired direction of contraction.

If the contact layer 140 is subjected to negative pressure, the holes 205 may contract, which can disrupt the debris. For example, the edges of the holes 205 may form cutting edges that can disrupt the debris. In some embodiments, the cutting edges may be defined by the perimeter 410 of each of the holes 205. If negative pressure is removed, for example, by venting the negative pressure, the contact layer 140 can expand back to a relaxed position. If the contact layer 140 is cycled between the contracted and relaxed positions, the contact layer 140 and the protrusions of the retainer layer (not shown) may mechanically disrupt the debris further. In some embodiments, the negative pressure applied by the negative-pressure source 105 may be cycled rapidly. For example, negative pressure may be supplied for a few seconds and then vented for a few seconds, causing a pulsation of negative pressure in a sealed environment. The pulsation of the negative pressure can pulse the nodules, which can cause further disruption of the debris. Such contraction of the contact layer 140 and holes 205 in combination with the action of the one or more debriding agents at the tissue site can not only advantageously allow for increased debridement at the tissue site but also advantageously result in co-action or synergy in debriding the tissue site and debris.

Contraction can refer to both vertical contraction and lateral contraction. The material, the void space percentage, the perforation shape factor, the firmness factor, the dimensions of the holes 205, and the strut angle may influence or control the direction of contraction. For example, in some embodiments, one or more of the void space percentage, the perforation shape factor, or the strut angle can cause the contact layer 140 to contract along the second orientation line 310 perpendicular to the first orientation line 305 as shown in FIG. 6. If the contact layer 140 is positioned on a tissue site, the contact layer 140 may contract in the direction of the lateral force 415 toward the first orientation line 305. In some embodiments, the holes 205 may be circular, the strut angle may be approximately 37°, the void space percentage may be about 54%, the firmness factor may be about 5, the shape factor may be about 1, and the diameter may be about 5 millimeters. If the contact layer 140 is subjected to a negative pressure of about −125 mmHg, the contact layer 140 can assert a lateral force 415 in the direction of approximately 11.9 N. If the diameter of the holes 205 is increased to about 20 millimeters, the void space percentage changed to about 52%, the strut angle changed to about 52°, and the perforation shape factor and the firmness factor remain the same, the lateral force can be decreased to about 6.5 N.

In some embodiments, dimensions of the holes 205 may be selected to permit flow of particulates through the holes 205. In some embodiments, for example, the effective diameter of the holes 205 may be selected based on an anticipated size of solubilized debris to be lifted from a tissue site. Dimensions may also be selected to allow larger debris and block smaller debris. In some examples, some or all of the debris may be drawn through the holes 205 and collected in the container 115. Optionally, the size of the holes 205 may differ on successive applications of the dressing 110. For example, the dimensions of the holes 205 may be decreased as the size of the debris decreases. Sequentially decreasing size of the holes 205 may also aid in fine tuning a level of tissue disruption to the debris during the treatment of a tissue site.

The dimensions of the holes 205 can also influence fluid movement in the contact layer 140 and the dressing 110. For example, the contact layer 140 can channel fluid in the dressing 110 toward the holes 205 to aid in the disruption of the debris on the tissue site. Variation of the dimensions of the holes 205 can vary how fluid is moved through the dressing 110 with respect to both the removal of fluid and the application of negative pressure.

In some embodiments, such as the example of FIG. 7, stresses on the debris may be focused at the vertices of the holes 205. Suitable characteristics of the contact layer 140 of FIG. 7 may include a strut angle of approximately 66°, a void space percentage of about 55%, a firmness factor of about 5, a perforation shape factor of about 1.07, and an effective diameter of about 5 millimeters. If the contact layer 140 of FIG. 7 is subjected to a negative pressure of about −125 mmHg, the lateral force 415 of the contact layer 140 may be about 13.3 N. If the effective diameter of the holes 205 is increased to 10 millimeters, the lateral force 415 may be decreased to about 7.5 N.

In some embodiments, the debris can be removed from a surface of the tissue site during dressing changes. For example, the contact layer 140 may be removed and disrupted debris may be removed by wiping away the debris. In other embodiments, the contact layer 140 may disrupt the debris so that the debris can be removed by negative pressure.

In some embodiments, instillation therapy may be combined with negative-pressure therapy. For example, the solution source 165 may be fluidly coupled to the contact layer 140 in some embodiments. Following a period of negative-pressure therapy, the therapy system 100 may operate the solution source 165 to provide fluid to the sealed environment. In some embodiments, the solution source 165 may provide fluid while the sealed environment is vented. In other embodiments, the sealed environment may not be vented, and the negative pressure in the sealed environment may draw instillation fluid from the solution source 165 into the sealed environment. The fluid removed may also comprise one or more of at least a portion of one or more debriding agents, at least a portion of the polymer and at least a portion of any further components, such as thickening agents and/or drying agents, of the debriding matrix.

In some embodiments, the solution source 165 may provide a volume of fluid to the sealed environment. In some embodiments, the volume of fluid may be the same as a volume of the sealed environment. In other embodiments, the volume of fluid may be smaller or larger than the sealed environment. Instilling solution into the sealed environment can increase pressure above ambient pressure, for example to between about 0 mmHg and about 15 mmHg and, more specifically, about 5 mmHg. In some embodiments, fluid provided by the solution source 165 may remain in the sealed environment for a prescribed dwell time. In some embodiments, the dwell time may be about 5 minutes. In other embodiments, the dwell time may be longer or shorter as prescribed. For example, the dwell time may be zero.

At the conclusion of the dwell time, the negative-pressure source 105 may be operated to draw the instillation fluid into the container 115, completing a cycle of therapy. As the instillation fluid is removed from the sealed environment with negative pressure, negative pressure may also be supplied to the sealed environment, starting another cycle of therapy.

In some embodiments, the methods described herein, for example using the therapy system 100, may be used in conjunction with other tissue removal and debridement techniques. For example, further mechanical and/or enzymatic debridement process may be used to remove further portions of the debris, for example, before positioning of the dressing 110 and/or after supplying negative pressure and/or fluid to the tissue site. Additionally or alternatively, sharp debridement may also be used as necessary for removal at least a portion of the debris, for example, before positioning of the dressing 110 and/or after supplying negative pressure and/or fluid to the tissue site. Sharp debridement may include, but is not limited to the use of a scalpel, scissor or other sharp instrument in debriding a tissue site.

The systems, apparatuses, and methods described herein may provide significant advantages. For example, in some embodiments, the therapy system 100 can provide mechanical movement and debriding agents in combination with negative pressure, instillation solution, or both, to solubilize, debride, and/or remove the debris. Thus, mechanical debridement and enzymatic debridement may be provided in combination. In some embodiments, cyclical application of instillation therapy and negative pressure therapy may cause the contact layer 140 to float and change position relative to the debris. For example, negative pressure may be applied to the sealed environment during a negative-pressure therapy cycle. Following the conclusion of the negative-pressure therapy cycle, instillation fluid may be supplied during the instillation therapy cycle. The instillation fluid may cause the contact layer 140 to float relative to the debris. The position change may cause the contact layer 140 to engage a slightly different portion of the debris during the next negative-pressure therapy cycle, aiding disruption of the debris.

Additionally or alternatively, the dressing 110 may allow more thorough slough removal. The dressing 110 may allow improved slough removal through improved contact of the dressing 110 with a tissue site, e.g., a wound bed, under negative pressure. The dressing 110 may provide a solution to de-sloughing the tops of macro-deformation formed on the wound bed during negative pressure therapy.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 110, the container 115, or both may be eliminated or separated from other components for manufacture or sale. In other example configurations, the controller 130 may also be manufactured, configured, assembled, or sold independently of other components. Additionally or alternatively, the retainer layer 145 may be omitted in some embodiments. For example, the holes 205 may be recesses in the contact layer 140, and tissue can be drawn into the recesses under negative pressure. Projections can be disposed within recesses in some examples.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A dressing for treating a tissue site with negative pressure, the dressing comprising:

a contact layer comprising a first manifold having a plurality of holes through the first manifold; and a retainer layer comprising a second manifold having a planar surface configured to be positioned adjacent to and in contact with a surface of the contact layer; and a plurality of projections coupled to the planar surface and extending from the planar surface at ambient pressure, the plurality of projections being formed from an open-cell, reticulated foam, and each of the plurality of projections configured to protrude into a respective hole of the plurality of holes of the contact layer at ambient pressure.

2. The dressing of claim 1, wherein the retainer layer is more compressible than the contact layer.

3. The dressing of claim 1, wherein the plurality of projections are complementary to the plurality of holes.

4. The dressing of claim 1, wherein at least some of the plurality of projections have a tapered end disposed within the plurality of holes.

5. The dressing of claim 1, wherein one or more of the plurality of projections have a ragged outer surface.

6. The dressing of claim 1, wherein at least one of the plurality of holes has a diameter between 1 millimeter (mm) and 30 mm and a height between 1 mm and 30 mm.

7. The dressing of claim 1, wherein the retainer layer comprises a foam having an average pore size between 10 pores per inch (ppi) and 80 ppi.

8. The dressing of claim 1, wherein the contact layer and retainer layer are connected as an integral layer.

9. The dressing of claim 1, wherein the dressing further comprises a cover layer configured to be positioned adjacent to the retainer layer.

10. The dressing of claim 1, wherein the plurality of holes are configured to collapse from a relaxed position to a contracted position in response to negative pressure.

\* \* \* \* \*